(12) United States Patent
Indig

(10) Patent No.: US 6,914,078 B2
(45) Date of Patent: Jul. 5, 2005

(54) TRIARYLMETHANE DERIVATIVES AND THEIR USE AS PHOTOCHEMOTHERAPEUTIC AGENTS

(75) Inventor: Guilherme L. Indig, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 229 days.

(21) Appl. No.: 10/374,770

(22) Filed: Feb. 25, 2003

(65) Prior Publication Data

US 2003/0229147 A1 Dec. 11, 2003

Related U.S. Application Data

(63) Continuation-in-part of application No. 09/863,149, filed on May 22, 2001, now abandoned, which is a continuation-in-part of application No. 09/753,472, filed on Jan. 3, 2001, now abandoned.

(51) Int. Cl.[7] .............................................. A61K 31/13
(52) U.S. Cl. ..................... 514/641; 514/638; 564/641; 564/638; 564/270; 564/271; 564/315; 564/427; 564/305
(58) Field of Search ................................ 514/641, 638; 564/270, 271, 315, 427, 305

(56) References Cited

U.S. PATENT DOCUMENTS

2002/0123530 A1    9/2002  Indig

OTHER PUBLICATIONS

Indig, G., et al., "Effect of Molecular Structure on the Phototoxicity of Triarylmethane Dyes Towards Tumor and Normal Cells," Abstract, 30th Annual Meeting of the American Society for Photobiology, Quebec City, Canada, Jul. 13–17, 2002.

(Continued)

Primary Examiner—Samuel Barts
(74) Attorney, Agent, or Firm—Foley & Lardner LLP

(57) ABSTRACT

Disclosed are compounds having one of the following structures:

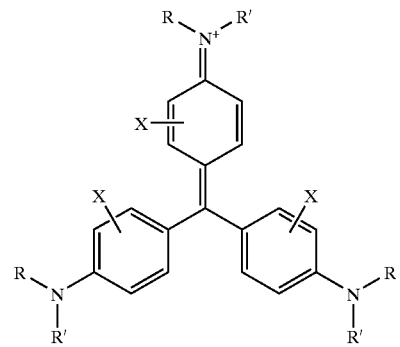

Formula I

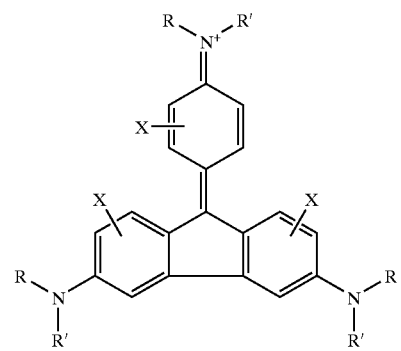

Formula II wherein R and R' are hydrogen or substituted or unsubstituted $C_1$ to $C_6$ linear or branched alkyl, and at least one X is a halogen atom, pharmaceutical compositions containing the compounds as active ingredients, and methods for using the compounds in the photodynamic treatment of cancers.

26 Claims, 5 Drawing Sheets

OTHER PUBLICATIONS

Kandela, Irawati K., et al., "Effect of Molecular Structure on the Selective Phototoxicity of Triarylmethane Dyes Towards Tumor Cells," *Journal of Pharmaceutical Sciences*, vol. 89, No. 1, Jan. 2000, and *Photochem. Photobiol. Sci.*, pp. 309–314, 2002.

Fiedorowicz, M. et al., "Efficient Photodynamic Action of Victoria Blue BO Against the Human Leukemic Cell Lines K–562 and TF–1," *Photochemistry and Photobiology*, vol. 58, No. 3, pp. 356–361, 1993; published by American Society for Photobiology.

Lewis, M. R. et al., "The Tumor–Inhibitory Activity of Diaryl– and Triarylmethane Dyes," *Cancer Research*, vol. 13, pp. 130–136, 1953.

Morgan, A. R. et al., "Synthesis and in vivo Activity of Some Porphyrindione Derivatives with Potential in Photodynamic Therapy," *Journal of Photochemistry and Photobiology, B: Biology*, vol. 6, pp. 133–141, 1990; published by Elsevier Sequoia/Printed in The Netherlands.

Morgan, A. R. et al., "Diels–Alder Adducts of Vinyl Porphyrins: Synthesis and in Vivo Photodynamic Effect against a Rat Bladder Tumor," *J. Med. Chem.*, vol. 33, pp. 1258–1262, 1990; published by American Chemical Society.

Morgan, A. R. et al., "Tin Etiopurpurin Dichloride–Sensitized Lipid Photooxidation of Erythrocyte Membranes," *Photochemistry and Photobiology*, vol. 52, No. 5, pp. 987–991, 1990; published by Pergamon Press plc/Printed in Great Britain.

Oseroff, A. R., "Cationic Sensitizers, Combination Therapies, and New Methodologies," *Photodynamic therapy: Basic principles and clinical applications*, pp. 79–96, 1992; published by Dekker, New York.

Patel, J. et al., "Design of Novel Analogs of Victoria Blue BO (VBBO) for Photodynamic Therapy," *Abstracts of Papers of the American Chemical Society*, vol. 203, Apr. 5–10, 1992, San Francisco, California.

Riley, J. F., M.D., "Retardation of Growth of a Transplantable Carcinoma in Mice Fed Basic Metachromatic Dyes," *Cancer Resaerch*, vol. 8, pp. 183–188, 1948.

Wadwa, K. et al, "Cationic Triarylmethane Photosensitizers for Selective Photochemotherapy: Victoria Blue–BO, Victoria Blue–R and Malachite Green," *Advances in Photochemotherapy*, vol. 997, pp. 154–161, 1988.

| | HT-29 (adenocarcinoma cells) | CV-1 (normal kidney cells) | Partition Coefficient (1-octanol/H₂O) | Dye Structure |
|---|---|---|---|---|
| EV⁺ | | | 237 ± 8 | |
| VPBBO⁺ | | | 180 ± 19 | |
| VBR⁺ | | | 39 ± 5.0 | |
| CV⁺ | | | 2.21 ± 0.06 | |
| I | | | 2.15 ± 0.15 | |
| II | | | 1.82 ± 0.08 | |
| III | | | 1.63 ± 0.06 | |
| IV | | | 0.77 ± 0.01 | |
| V | | | 0.59 ± 0.05 | |
| VI | | | 0.21 ± 0.01 | |

FIG. 1

TRIARYLMETHANE DERIVATIVES AND THEIR USE AS PHOTOCHEMOTHERAPEUTIC AGENTS

CROSS-REFERENCES TO RELATED APPLICATIONS

This application claims priority as a continuation-in-part application of U.S. patent application Ser. No. 09/863,149, filed May 22, 2001 now abandoned, which is a continuation-in-part application of U.S. patent application Ser. No. 09/753,472, filed Jan. 3, 2001 now abandoned. The entire disclosure of U.S. patent application Ser. No. 09/863,149 and the entire disclosure of U.S. patent application Ser. No. 09/753,472 are incorporated herein by reference and for all purposes.

FIELD OF THE INVENTION

The invention is directed to compositions and methods for treating cancer and more specifically to compositions and methods of treating cancer using triarylmethane dyes as photochemotherapeutic agents. The invention is also directed to compositions and methods of purging cancerous cells from non-cancerous cells in autologous bone marrow grafts.

BACKGROUND OF THE INVENTION

It is known that cancerous cells, such as tumor cells and leukemia cells, can be selectively purged from non-cancerous cells by photochemical methods. These methods are particularly useful in purging leukemia cells from a bone marrow graft before bone marrow transplantation. For instance, Merocyanine 540 (MC-540), a photosensitizing dye, has been used in photochemical purging of a patient's own (i.e., autologous) bone marrow graft. The effectiveness of MC-540-mediated photochemical purging, however, differs markedly in different leukemia cell lines.

Yamazaki and Sieber, found that the selective lethality of MC-540 for leukemia cells could be synergistically increased by using MC-540 in conjunction with an alkyl-lysophospholipid, rac-2-methyl-1-octadecyl-glycero-(3)-phosphocholine (ET-18-OCH$_3$). See *Bone Marrow Transplantation*, 19, 629 (1997). These authors found that when photodynamic therapy (PDT) with MC-540 was followed by incubating the cells in ET-18-OCH$_3$, the MC-540-mediated photoinactivation of leukemia cells was synergistically enhanced, while the treatment only minimally reduced the survival of normal granulocyte-macrophage progenitors.

On the basis of a comprehensive investigation involving more than 200 cell lines/types of melanoma, adenocarcinoma, transitional cell carcinoma, squamous cell carcinoma, and normal epithelial cells, Chen has demonstrated that enhanced mitochondrial membrane potential is a prevalent cancer cell phenotype. *Ann. Rev. Cell Biol.*, 4, 155 (1988). Only approximately 2% of all cells tested so far disobey this apparently dominant precept. Higher electric potentials have also been observed in the plasma membrane of a variety of carcinoma cells as compared to normal epithelial cells. Because cell and mitochondrial membrane potentials are negative inside, extensively conjugated cationic molecules displaying appropriate structural features can be electrophoretically driven through these membranes and accumulate into the cytosol and inside cell mitochondria. The mitochondrial membrane potential is typically more than 60 mV higher in carcinoma cells than in normal epithelial cells. As a result, a number of cationic dyes preferentially accumulate and are retained in a variety of tumor cells, presumably because the mitochondria of these cells are not capable of excreting the dyes with the same efficiency as normal cells.

The preferential uptake and retention of a variety of extensively conjugated cationic compounds by tumor cells have motivated the examination of mitochondrial targeting as a relevant therapeutic strategy for both chemotherapy and photochemotherapy of neoplastic diseases. However, the structural parameters that control the accumulation of these compounds into cell mitochondria are not entirely understood, and the lack of a robust model to describe the relationship between molecular structure and mitochondrial accumulation has prevented mitochondrial targeting from becoming a more dependable therapeutic strategy. Described herein is a method of treating cancer that utilizes cationic, triarylmethane dye derivatives. In some of the methods disclosed herein the triarylmethane dye is a halogenated cationic triarylmethane dye. While the invention is not limited to a particular mode of action, it is thought that the destruction of tumor cells wrought by the method arises via selective accumulation of the dye in the mitochondria of tumor cells.

Since 1953, when Nussenzweig first described the inactivation of the protozoan parasite *Trypanosoma cruzi* (the vector responsible for Chagas' disease) by the cationic triarylmethane dye crystal violet (CV$^+$), this triarylmethane dye has been extensively used in blood banks in underdeveloped areas to prevent transfusion-associated transmission of Chagas' disease (American trypanosomiasis). See Nussenzweig, et al., *Hospital (Rio J)*, 44, 731 (1953). CV$^+$ does not cause severe side effects in patients who receive blood treated with it, nor are the functions of blood cells jeopardized as a result of the chemoprophylaxis. The safety of CV$^+$ is further demonstrated by its use as an anthelmintic, an antiseptic in umbilical cords of newborns and in burn patients.

SUMMARY OF THE INVENTION

One aspect of the invention provides compositions and methods for selectively killing cancer cells or inhibiting the growth of cancer cells in a mixture of cancerous and non-cancerous cells. Thus, in one aspect the invention provides compounds having structures represented by Formula I or Formula II, shown below, tautomers of the compound, pharmaceutically acceptable salts of the compounds, and pharmaceutically acceptable salts of the tautomers. The invention also provides pharmaceutical formulations that include the compounds, tautomers, pharmaceutically acceptable salts of the compounds, or pharmaceutically acceptable salts of the tautomers. The invention further provides methods for selectively killing cancer cells or inhibiting the growth of cancer cells in a mixture of cancerous and non-cancerous cells. The method includes contacting the mixture of cells with a pharmaceutically effective amount of a compound having a structure represented by Formula I or Formula II, a tautomer of the compound, a pharmaceutically acceptable salt of the compound, or a pharmaceutically acceptable salt of the tautomer. Compounds of Formula I and Formula II have the following structures:

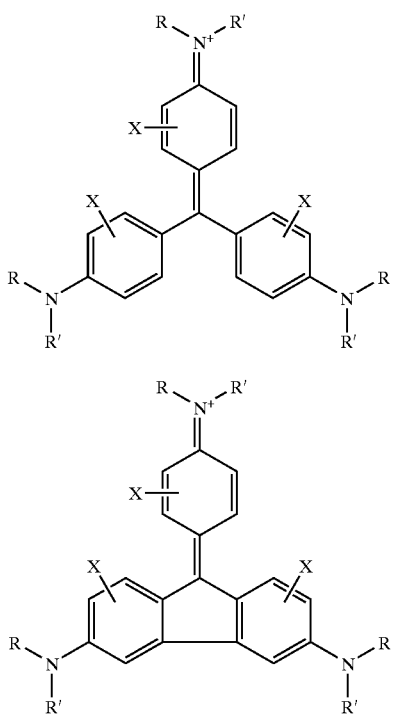

Formula I and

Formula II wherein each R and R' is independently selected from the group consisting of hydrogen and substituted or unsubstituted $C_1$–$C_6$ linear or branched alkyl groups, and each X is independently selected from the group consisting of hydrogen and halogen atoms, and further wherein at least one X in the compounds having the structure shown in Formula I is a halogen atom. Bromine and iodine are particularly suitable halogen atoms. In some embodiments X represents bromine. In other embodiments X represents iodine. Other suitable halogen atoms are chlorine and fluorine. In the method for selectively killing cancer cells or inhibiting the growth of cancer cells in a mixture of cancerous and non-cancerous cells, the cancer cells so treated are exposed to radiation of a suitable wavelength to photoactivate the compound, causing selective cancer cell death or selective cancer cell growth inhibition. The method can be used to treat any cancer cells for which the compounds of Formula I or II demonstrate selective phototoxicity relative to non-cancerous cells. For example, the method can be used to treat solid neoplastic tumors and circulating neoplasms including, but not limited to, leukemia, adenocarcinoma, and uterine sarcoma. The method may be used to selectively kill or inhibit the growth of cancer cells in vitro, in vivo, or ex vivo.

In one embodiment of the invention, the method is used to purge malignant cells from a mixture comprising malignant cells and non-malignant bone marrow cells. The method may be used to prepare autologous bone marrow transplants for reimplantation into the subject from which the transplant was taken. The subject will normally be a mammal (human or other mammal) suffering from a neoplasm involving the cells found in bone marrow, such as leukemia.

In other embodiments of the invention, the method is used to selectively destroy or inhibit the growth of solid tumors, including, but not limited to, tumors associated with adenocarcinoma and uterine sarcoma.

A second aspect of the invention provides pharmaceutical compositions for the photo-initiated treatment of neoplastic cell growth in mammals, including humans. The composition comprises a pharmaceutically effective amount of one or more compounds as described herein, in combination with a pharmaceutically-suitable diluent or carrier. A pharmaceutically effective amount of a compound is defined, for the purposes of this disclosure, as an amount suitable to provide selective destruction or selective growth inhibition of cancerous cells relative to non-cancerous cells when exposed to radiation of a suitable wavelength to photoactivate the compound.

It has been found that the compounds disclosed herein, which belong to a group of compounds known as cationic triarylmethane dyes (and referred to generally as "TAM$^+$" dyes) exhibit pronounced and unexpected phototoxicity towards cancerous cells and low toxicity toward normal, healthy cells. On the basis of the selectivity which the phototoxic effect of these compounds develops toward tumor cells as compared to normal cells, the principal advantage and benefit of the invention is that these triarylmethane dyes can be used in photodynamic therapy to destroy and/or inhibit the growth of cancer cells, while leaving non-cancerous cells viable. One use of the invention, therefore, is as a novel purging protocol to promote the elimination of residual tumor cells from autologous bone marrow grafts with minimum toxicity toward normal cells.

Additionally, many of the compounds described herein have absorbance maxima in the near infrared region. These compounds are well-suited for photodynamic therapy, especially in solid tumors, because near-infrared light penetrates tissues better than does shorter wavelength visible light.

The compounds of the present invention are also well suited for tumor detection and imaging applications. In various embodiments, halogen atoms located at one or more of the "X" positions of the dyes are radio-opaque or positron-emitting halogen atoms. In addition to acting as photochemotherapeutic agents, these compounds may be used as tumor-selective dyes. Such compounds permit the detection and precise localization of tumors using conventional imaging techniques or in positron emission tomography. Suitable halogen atoms for use in the compounds of the present invention include, but are not limited to, bromine and iodine.

Analogously, tumor-selective dyes may be used in molecular radiation (isotopic) therapy, that is, as radiopharmaceuticals in nuclear medicine applications. In this embodiment, halogen atoms located at one or more of the "X" positions of the dyes are radioactive halogen isotopes. In addition to acting as photochemotherapeutic agents, these compounds may be used for the treatment of cancer via the selective destruction of the neoplastic tissue by the ionizing radiation emitted by these isotopes. Suitable radioactive isotopes for use in the compounds of the present invention include, but are not limited to, Br-76, Br-77, I-123, I-125, and I-131.

Finally the advantages of selective phototoxicity, imaging capability, and radiation may be combined using the compounds and pharmaceutical compositions provided by the present invention. This result stems from the fact that while the substitution of hydrogen (or other light-atom) by bromine, iodine or other heavy-atom tends to enhance the photoreactivity of dyes in general, several isotopes of heavy-atoms are both radio-opaque and radioactive. Examples of such isotopes include, but are not limited to, Br-76, Br-77, I-123, I-125, and I-131. Therefore, some of the structural features that would enable a tumor-specific dye for use in tumor imaging and molecular radiation therapy (i.e. nuclear medicine) may also promote an enhancement in phototoxicity (or drug potency).

BRIEF DESCRIPTION OF THE DRAWINGS

FIG. 1 shows the phototoxicity of TAM$^+$ dyes towards tumor (HT-29) and normal (CV-1) cells. Colonies of HT-29 (left panels) and CV-1 (right panels) cells were incubated for 1 hour with 5 $\mu$M TAM$^+$ dyes, washed, and irradiated for 1 hour as described in Example 2, below. Twenty four hours after irradiation the cells were fixed with methanol and stained. Before irradiation, half of each petri dish was masked with black tape. The area protected from light is represented by the right-half of each panel. Upon irradiation, only the HT-29 cells were heavily destroyed when the 1-octanol/water partition coefficient (P) associated with the TAM$^+$ photosensitizer was equal or lower than 2.2. For the cases of TAM$^+$ dyes showing partition coefficient above that of CV$^+$ no tumor selectivity was observed. No phototoxic effects were observed upon irradiation of the cells in the absence of the TAM$^+$ dyes.

DETAILED DESCRIPTION OF THE INVENTION

Figure 2:
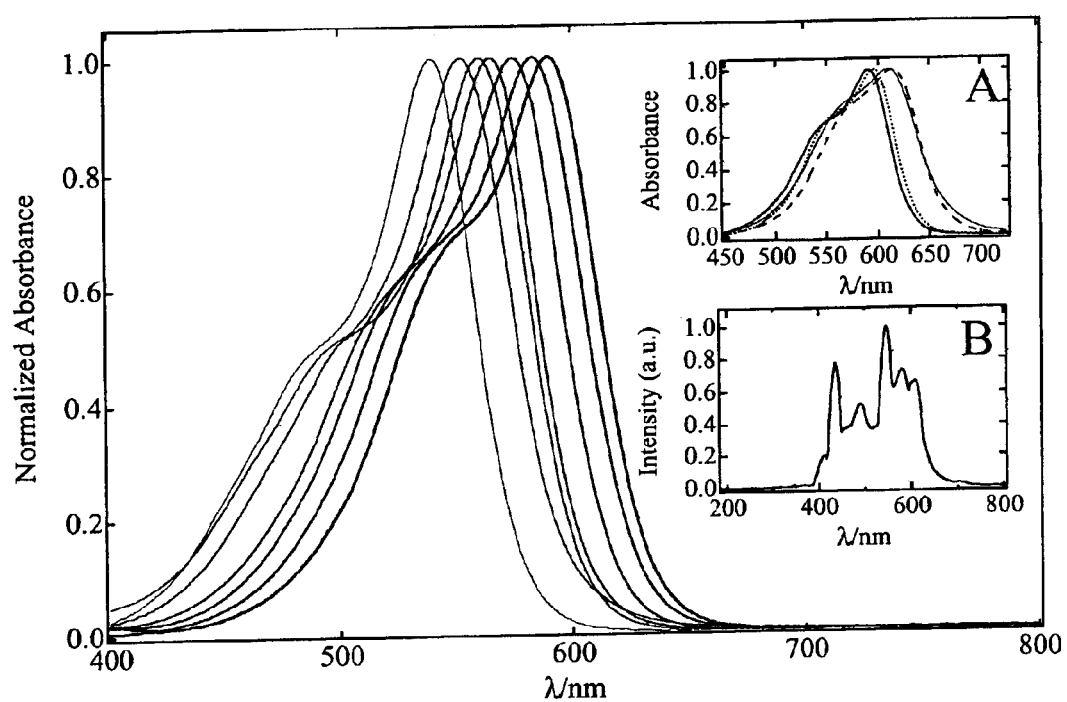
FIG. 2 shows the absorption spectra of CV$^+$ and its N-demethylated derivatives in water. From right to left, CV$^+$ (I); N,N,N',N',N'',N''-pararosaniline), N,N,N',N',N''-pararosaniline (II), N,N,N',N''-pararosaniline (III), N,N',N''-pararosaniline (IV), N,N'-pararosaniline (V), N,-pararosaniline (VI), and pararosaniline (VII). Inset A, absorption spectra of (from right to left): VPBBO$^+$ (dashed line), VBR$^+$ (solid line), EV$^+$ (dotted line), and CV$^+$ (solid line), all recorded in water. Inset B, emission profile of the light source used to irradiate the cells.

Extensively conjugated cationic molecules with appropriate structural features will accumulate in the mitochondria of living cells, a phenomenon typically more prominent in tumor cells than in normal cells. It has been found that a variety of tumor cells also retain pertinent cationic structures for longer periods of time compared to normal cells. While not being bound to a particular mode of action, the present methods utilize mitochondrial targeting as a selective therapeutic strategy of relevance for both chemotherapy and photochemotherapy of neoplastic diseases in general, and leukemia in particular.

The present invention is directed to the use of triarylmethane (TAM$^+$) dyes for photochemotherapy of neoplastic conditions. The TAM$^+$ dyes disclosed herein stain neoplastic cell mitochondria with efficiency and selectivity. Upon exposure to suitable wavelengths of energy, the dyes exhibit pronounced and selective phototoxicity toward neoplastic cells. As illustrated in the examples that follow, the TAM$^+$ dyes exhibit pronounced phototoxicity toward HT-29 adenocarcinoma cells. The same dyes show comparatively small toxic effects toward CV-1 normal kidney cells. On the basis of a comparative examination of chemical, photochemical, and phototoxic properties of the TAM$^+$ dyes, certain interdependencies between molecular structure and selective phototoxicity toward tumor cells have been identified. These structure-activity relationships provide useful guidelines for the methods of treatment described herein.

A first aspect of the invention provides a method of selectively killing cancer cells or selectively inhibiting the growth of cancer cells in a mixture of cancerous and non-cancerous cells. In this method the mixture of cancerous and non-cancerous cells is exposed to a pharmacologically effective amount of a TAM$^+$ dye having one of the following formulas, or a mixture of TAM$^+$ dyes having one of the following formulas:

Formula I

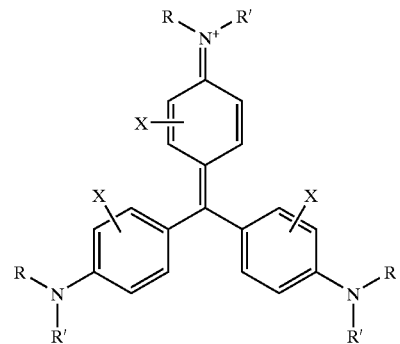

and

Formula II

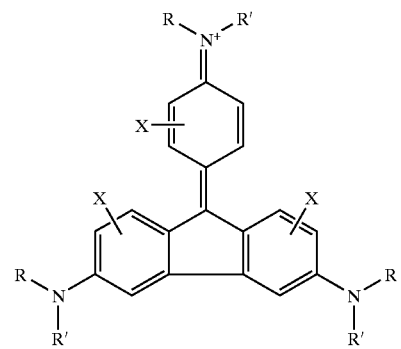

and pharmaceutically suitable salts thereof, wherein each R and R' is independently selected from the group consisting of hydrogen and substituted or unsubstituted $C_1$–$C_6$ linear or branched alkyl groups, and each X is independently selected from the group consisting of hydrogen and halogen atoms. For compounds having the structure shown in Formula I above, at least one X in the compounds is a halogen atom. In some compounds at least one of the R or R' groups is an alkyl group that is halogenated with at least one radio-opaque or radioactive halogen atom.

For the purposes of this disclosure, the structures represented by Formula I and Formula II above and all other structures provided in this disclosure are meant to cover the tautomeric forms of the structures as well as the structures explicitly depicted or described.

As the molecules represented by Formula I and Formula II above are salts, they may be associated with a variety of counterions, including, but not limited to, acetate, bicarbonate, bromide, chlorate, chloride, hypochlorite, perchlorate, iodate, iodide, formate, gluconate, citrate, phosphate, and tartrate ions.

TAM$^+$ dyes having the structure shown in Formula II are more rigid than their Formula I counterparts. These dyes absorb light in the visible and near infrared regions of the spectrum at wavelengths in the range of from 700 nm or about 700 nm to 950 nm or about 950 nm and this includes dyes that absorb light in the range of from 750 nm or about 750 nm to 900 nm or about 900 nm. In this spectroscopic region, light penetration into living tissue is close to maximal, making TAM$^+$ dyes having the structure shown in Formula II particularly suited for the treatment of relatively large solid tumors, which require deep penetration of the light into the tumoral mass.

In the compounds shown above, bromine and iodine are examples of suitable halogen atoms. Other suitable halogens include chlorine and fluoride.

Suitable $C_1$–$C_6$ alkyl groups include, but are not limited to, methyl groups, ethyl groups, propyl groups, isopropyl groups, butyl groups, isobutyl groups, sec-butyl groups, butyl pentyl groups, tert-pentyl groups, neopentyl groups, and hexyl groups.

In some embodiments, each of the R and R' groups is a hydrogen. In other embodiments, five of the R and R' groups are hydrogen atoms and the other R or R' group is a $C_1$–$C_6$ linear or branched alkyl group such as a methyl group. In other embodiments, four of the R and R' groups are hydrogen atoms and the other two R or R' groups are $C_1$–$C_6$ linear or branched alkyl groups such as methyl groups. In other embodiments, three of the R and R' groups are hydrogen atoms and the other three R or R' groups are $C_1$–$C_6$ linear or branched alkyl groups such as methyl groups. In other embodiments, two of the R and R' groups are hydrogen atoms and the other four R or R' groups are $C_1$–$C_6$ linear or branched alkyl groups such as methyl groups. In other embodiments, one of the R or R' groups is a hydrogen atom and the other five R or R' groups are $C_1$–$C_6$ linear or branched alkyl groups such as methyl groups.

The alkyl groups may be substituted or unsubstituted alkyl groups. Suitable substituents for the alkyl groups may be any substituent that does not eliminate the selective phototoxicity of the TAM$^+$ dyes. Examples of substituents include, but are not limited to, hydroxyl groups, amino groups, and halogens.

The compounds may be monohalogenated or multiply halogenated. In some embodiments the compounds are dihalogenated. As shown in the structures above, the compounds of Formula I and Formula II may be substituted by an "X" group at any suitable and compatible position on each of the phenyl rings in the compound.

In some compounds having the structures shown by Formulas I or II, only one of the "X" positions is halogenated and the remaining "X" positions are occupied by hydrogen atoms. In other compounds having the structures shown by Formulas I and II, two of the "X" positions are halogenated and the remaining "X" positions are occupied by hydrogen atoms. In other compounds having the structures shown by Formulas I and II, three of the "X" positions are halogenated and the remaining "X" positions are occupied by hydrogen atoms. In other compounds having the structures shown by Formulas I and II, four of the "X" positions are halogenated and the remaining "X" positions are occupied by hydrogen atoms. In other compounds having the structures shown by Formulas I and II, five of the "X" positions are halogenated and the remaining "X" positions are occupied by hydrogen atoms. In other compounds having the structures shown by Formulas I and II, six of the "X" positions are halogenated and the remaining "X" positions are occupied by hydrogen atoms. In some compounds having the structure shown by Formula II, all of the "X" positions are occupied by hydrogen atoms.

In various embodiments, the compounds are prepared with a radio-opaque and/or positron emitting halogen atom at one or more of the "X" positions in their molecular structure. These compounds may be used as tumor-selective dyes. These compounds may be used to treat cancer via the selective destruction of the neoplastic tissue by the nuclear radiation emitted by these isotopes, including, but not limited to gamma and beta radiation.

In some compounds having the structures shown by Formula I or II, one of the "X" positions is a radioactive and/or a radio-opaque and/or positron emitting halogen atom. In other compounds having the structures shown by Formula I or II, two of the "X" positions are radioactive and/or radio-opaque and/or positron emitting halogen atoms. In other compounds having the structures shown by Formulas I or II, three of the "X" positions are radioactive and/or radio-opaque and/or positron emitting halogen atoms. In other compounds having the structures shown by Formulas I or II, four of the "X" positions are radioactive and/or radio-opaque and/or positron emitting halogen atoms. In other compounds having the structures shown by Formulas I or II, five of the "X" positions are radioactive and/or radio-opaque and/or positron emitting halogen atoms. In other compounds having the structures shown by Formulas I or II, six of the "X" positions are radioactive and/or radio-opaque and/or positron emitting halogen atoms.

As noted above, the R and $R^1$ groups on the TAM$^+$ dyes may be substituted alkyl groups. Halogen atoms make useful substituents, particularly halogens that are radio-active, radio-opaque, and/or positron emitting. The same halogen atoms and isotopes that may be present at the "X" positions of the structures represented by Formula I and Formula II may also be present in one or more of the halogenated alkyl groups at the R and $R^1$ positions. In some compounds having the structures shown by Formula I or II, one or more of the R or R' groups comprises a singly or multiply halogenated alkyl group. In other compounds having the structures shown by Formula I or II, two of the R or R' groups comprise singly or multiply halogenated alkyl groups. In other compounds having the structures shown by Formula I or II, three of the R or R' groups comprise singly or multiply halogenated alkyl groups. In other compounds having the structures shown by Formula I or II, four of the R or R' groups comprise single or multiply halogenated alkyl groups. In other compounds having the structures shown by Formula I or II, five of the R or R' groups comprise single or multiply halogenated alkyl groups. In other compounds having the structures shown by Formula I or II, six of the R or R' groups comprise single or multiply halogenated alkyl groups.

In one embodiment of the invention, the TAM$^+$ dye has the following structure:

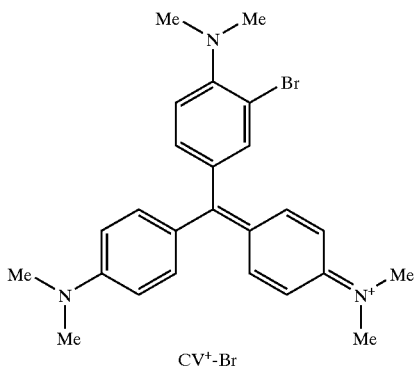

CV⁺-Br where "Me" represents a methyl group. This compound is 3'-bromocrystal violet and is designated "CV⁺—Br." This is an example of a compound of Formula I where one X is Br and all six R and R' groups are $C_1$–$C_6$ linear alkyl groups (e.g. methyl groups).

In another embodiment of the invention, the TAM⁺ dye has the following structure:

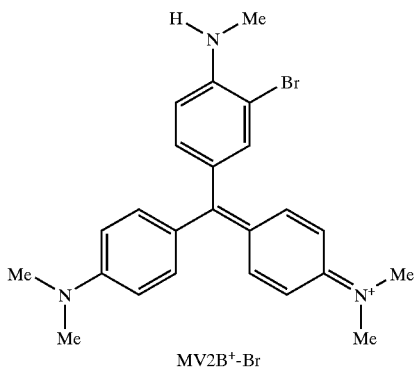

MV2B⁺-Br where "Me" represents a methyl group. This compound is 3'-bromomethyl violet 2B and is designated "MV2B⁺—Br." This is an example of a compound of Formula I where one X is Br, one R or R' group is hydrogen, and five R and R' groups are $C_1$–$C_6$ linear alkyl groups (e.g. methyl groups).

In yet another embodiment of the invention the TAM⁺ dye has the following structure:

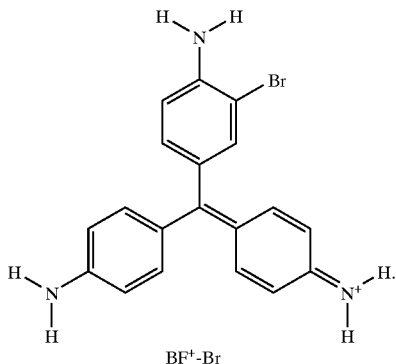

BF⁺-Br

This compound is 3'-bromobasic fuchsin and is designated "BF⁺—Br." This is an example of a compound of Formula I where one X is Br and all six R and R' groups are hydrogens.

In yet another embodiment of the invention, the TAM⁺ dye has the following structure:

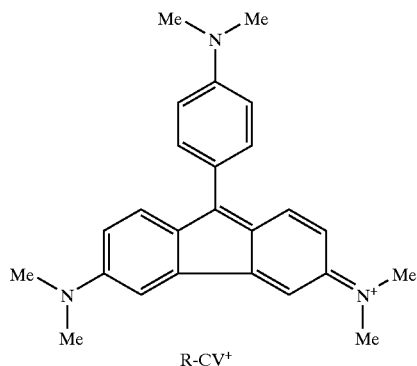

R-CV⁺ where "Me" represents a methyl group. This compound is 3,6-bis-dimethylamino-9-(4-dimethylamino-phenyl)-fluoren-9-ylium and is designated "R—CV⁺." This is an example of a compound of Formula II where no X positions are halogens and all six R and R' groups are $C_1$–$C_6$ linear alkyl groups (methyl groups).

Once a mixture of cancerous and non-cancerous cells has been exposed to a TAM⁺ dye or dyes, it is exposed to light of a suitable wavelength to photoactivate the dye, causing selective destruction or selective growth inhibition of the cancerous cells. One of skill in the art will understand that the range of wavelengths suitable to photoactivate the compounds will vary depending upon the particular compound being used. In some embodiments of the invention, the light is visible light having wavelengths in the range of from 400 nm or about 400 nm to 750 nm or about 750 nm. This includes light having wavelengths in the range of from 450 nm or about 450 nm to 600 nm or about 600 nm, and further includes light having wavelengths in the range of from 500 nm or about 500 nm to 750 nm or about 750 nm. The visible light may be provided by conventional fluorescent bulbs and other light sources well known in the art. Examples include, but are not limited to, cool white, warm white, and daylight fluorescent lamps, pulsed xenon lamps, quartz halogen lamps, Nd-YAG and dye lasers, and light emitting diodes (LEDs).

In other embodiments, the TAM⁺ dyes are photoactivated by near infrared light having wavelengths in the range of from 750 nm or about 750 nm to 1,000 nm or about 1,000 nm. This includes light having wavelengths in the range of from 750 nm or about 750 nm to 950 nm or about 950 nm and further includes light having wavelengths in the range of from 750 nm or about 750 nm to 900 nm or about 900 nm. Examples of suitable sources for infrared light include, xenon, mercury, and xenon-mercury lamps, optical parametric oscillator (OPO) and dye lasers, and light emitting diodes (LEDs).

The mixture of cancerous and non-cancerous cells should be exposed to the light of a suitable wavelength to photoactivate the TAM⁺ dyes for a time sufficient to selectively destroy or inhibit the growth of at least some of the cancerous cells relative to the non-cancerous cells. One of skill in the art will recognize that the time of exposure will vary depending upon a variety of factors, including the type of cancer being treated, the TAM⁺ dye or dyes being used, and the light source being used. Thus, the time of exposure should be a period of time suitable to achieve a therapeutic response from the dyes. Typically, the period of exposure will last from about 1 minute to about ninety minutes, possibly from 1 minute or about 1 minute to sixty minutes or about sixty minutes, or from 1 minute or about 1 minute to 30 minutes or about 30 minutes, or even from 1 minute or about 1 minute to 10 minutes or about 10 minutes.

A second aspect of the invention provides pharmaceutical compositions that selectively destroy or inhibit the growth of cancerous cells relative to non-cancerous cells in a mixture of cancerous and non-cancerous cells. Such compositions comprise a pharmaceutically effective amount of one or more of the TAM$^+$ dyes of Formula I or Formula II described above, and, optionally, a pharmaceutically-suitable diluent or carrier. Examples of suitable diluents include water, phosphate buffered saline, water-ethanol mixtures, ethanol, water-polyethylene glycol (PEG), and water-dimethylacetamide (DMA) mixtures. Examples of suitable carriers include cyclodextrins, liposomes, albumins, such as human albumin, and lipoproteins, such as human lipoproteins. One of skill in the art will recognize that a pharmaceutically effective amount will vary depending on a variety of factors, including the type of cancer being treated and the particular TAM$^+$ dye being used. In various embodiments, a pharmaceutically effective amount will range from about 0.1 mg per liter of cell suspension or patient blood to about 500 mg per liter of cell suspension or patient blood. This includes embodiments wherein a pharmaceutically effective amount is from about 1 mg per liter of cell suspension or patient blood to about 250 mg per liter of cell suspension or patient blood and further includes embodiments wherein a pharmaceutically effective amount is from about 0.1 mg per liter of cell suspension or patient blood to about 100 mg per liter of cell suspension or patient blood.

Without intending to be bound to any particular theory of the invention, it is hypothesized that the pharmaceutical compositions and methods for the selective destruction of cancerous cells, disclosed and demonstrated herein, utilize mitochondrial targeting as a selective therapeutic strategy of relevance for photochemotherapy of neoplastic diseases in general. It is further hypothesized that the demonstrated tumor selectivity displayed by the compounds of this invention is primarily dependent on the lipophilic/hydrophilic character of the "mitochondrial" photosensitizer. Previous studies have indicated that while selective phototoxicity towards tumor cells can be easily achieved with TAM$^+$ dyes showing 1-octanol/water partition coefficients close to that of the highly specific fluorescent mitochondrial marker Rh 123$^+$, this selectivity is also easily lost upon increasing the lipophilic character of the "mitochondrial" photosensitizer. This suggests that for tumor selectivity to take place, the photosensitizer must localize in energized mitochondria with high specificity.

The present methods are further illustrated by the following non-limiting examples.

EXAMPLE 1

General Methods for the Preparation of Halogenated Triarylmethane Dyes

Preparation of Triarylmethane Dyes:

Chlorine salts of the triarylmethane dyes ethyl violet (EV$^+$), victoria blue R (VBR$^+$), victoria pure blue BO (VPBBO$^+$) from Aldrich Chemical (Milwaukee, Wis.), and crystal violet (CV$^+$) from Sigma (St. Louis, Mo.) were recrystallized from methanol and dried under vacuum. The purity of recrystallized TAM$^+$ dyes was assessed by thin-layer chromatography (TLC, silica gel, methanol-acetic acid 95:5, vol/vol).

The TAM$^+$ dyes according to the present invention can also be synthesized using two approaches. First, they can be synthesized via enzymatic N-dealkylation of the next-higher homolog in the series. See Gadelha et al., *Chem-Biol. Interactions,* 85, 35 (1992), incorporated herein by reference. Specifically, starting with the parent per-alkylated compound, alkyl groups can be sequentially removed using horseradish peroxidase. Because the reaction requires $H_2O_2$ to proceed, the extent of dealkylation is controlled by limiting the initial concentration of $H_2O_2$ and allowing the reaction to go to completion. Therefore, the experimental conditions can be tailored to maximize the yield of each product of interest, thereby greatly facilitating the isolation of the product via HPLC. Second, the TAM$^+$ dyes can be synthesized via sequential alkylation of basic fuchsin (also referred to as pararosaniline) using iodoalkanes as alkylating agents. For example, N-methylpararosaniline can be easily prepared from basic fuchsin using iodomethane as the alkylating agent. To this end, 10 ml of iodomethane (160 mmol) is slowly added to 40 ml of a stirred methanol solution of basic fuchsin (0.813 g, 2.51 mmol), the reaction mixture is kept under reflux, and the reaction progress followed by HPLC (reversed phase $C_{18}$ column; 70% acetonitrile-30% 20 mM aqueous $NH_4Cl$ as eluent). The final reaction products are subsequently dried through roto-evaporation and purified via HPLC.

More rigid analogs such as compounds of Formula II are prepared via covalent linking of two TAM$^+$ aromatic rings at the ortho position. The synthesis of such analogs may be accomplished using a procedure such as that disclosed in U.S. Pat. No. 3,344,189, which is incorporated herein by reference. Briefly, a suitable amount of the parent dye is dissolved in 85% sulfuric acid and the reaction mixture is slowly heated and kept at 205° C. for about 30 minutes. After the reaction is completed, the reaction mixture is cooled, poured onto ice, and the acid partially neutralized with aqueous ammonia. Sodium dithionite is subsequently added to reduce the dye to its respective leuco form. In this step, the acid remaining in solution is neutralized. The precipitate formed in this step is filtered, washed with water, and dried. This intermediate (leuco) compound is purified by recrystallization from toluene and subsequently oxidized to the respective carbinol base by treatment with lead peroxide in a mixture of glacial acetic acid and sulfuric acid. After four hours at room temperature, the lead sulfate is filtered off, and the carbinol base precipitated with sodium hydroxide. After recrystallization of the carbinol base, this last intermediate is finally converted to the chloride salt of the product with diluted hydrochloric acid.

The desired products are isolated via reversed-phase HPLC, using water-acetonitrile mixtures as eluent. In some separations, the presence of a strong electrolyte (e.g., $HClO_4$ or $NH_4Cl$) in the elution solution is required. Preference is given to isocratic elution with 70% acetonitrile, 30% 20 mM aqueous $NH_4Cl$ as eluent.

Preparation of Halogenated Triarylmethane Dyes:

Halogenated compounds according to the present invention can be synthesized by treating the parent compound with a molecular halogen, such as molecular bromine. A general description of a halogenation process may be found in Kobayashi, et al., *J. Chem. Res.* (S), 215 (1977), which is incorporated herein by reference. Briefly, the TAM$^+$ dye is dissolved in glacial acetic acid and a solution of bromine, also in glacial acetic acid, is slowly added thereto. Other solvents, such as methanol, can also be used in this procedure. Generally, the dye solution is stirred at a controlled temperature and under a positive pressure of nitrogen during the addition of the bromine. The stoichiometry of the final products (or the degree of halogenation) is controlled by the initial concentration of reactants, temperature, and reaction time. Iodination reactions are performed using aqueous sodium hydrogen carbonate as solvent, instead of glacial acetic acid. A description of this process can be found in Vogel's Textbook of Practical Organic Chemistry, Fifth Edition, B. S. Furniss, A. J. Hannaford, P. W. G. Smith, and A. R. Tatchell; Longman Scientific & Technical; Singapore, 1989, which is incorporated herein by reference.

Side-chain halogenation can be achieved by treating the aromatic alkyl amine with bromine at high temperatures (typically at the boiling point of the solvent in which the reaction is run), preferably with simultaneous exposure of the reaction media to a bright light source. A general method for halogenating side-chains may be found in Vogel's textbook of Practical Organic Chemistry, Fifth ed., published by Longman Scientifice and Technical, Essex, England (1989), which is herein incorporated by reference.

EXAMPLE 2

Preferential Destruction of Adenocarcinoma Cells by Triarylmethane Dyes

Materials and Methods:

Reagents and Cell Culture Media:

Chlorine salts of ethyl violet ($EV^+$), victoria blue R ($VBR^+$), victoria pure blue BO ($VPBBO^+$) from Aldrich (Milwaukee, Wis.), and crystal violet ($CV^+$, also referred to as N,N,N',N',N'',N''-hexamethylpararosaniline) from Sigma Chemical Co. (St. Louis, Mo.) were recrystallized from methanol and dried under vacuum. The purity of recrystallized triarylmethanes was assessed by thin-layer chromatography (silica gel, methanol-acetic acid 95:5, v:v). Pararosaniline ($PA^+$, >98% pure), methanol, n-butanol, acetic acid, acetonitrile, hydrochloric acid, perchloric acid, silica gel (230–400 mesh Merck grade 9385) from Aldrich, horseradish peroxidase (HRP, type VI), sodium chloride, potassium chloride, sodium phosphate (monobasic and dibasic salts), potassium phosphate (monobasic), and trypan blue from Sigma, and ethanol from Pharmaco Products, Inc. (Brookfield, Conn.), were all of high purity grade and used as supplied. RPMI 1640 cell culture media, Dulbecco's phosphate-buffered saline (DPBS), fungizone (amphotericin B), penicillin, streptomycin, ethylenediaminetetraacetic acid (EDTA; tetrasodium salt) and trypsin (porcine) were obtained from Gibco (Rockville, Md.). Fetal bovine serum (FBS) was purchased from Atlanta Biologica (Norcross, Ga.). Water was distilled, deionized, and filtered prior to use (Millipore Milli-Q system; resistivity, 18 MΩ cm).

Instruments and Methods:

Spectrophotometric studies were performed with a Shimadzu UV-2101PC spectrophotometer. High-Performance Liquid Chromatography (HPLC) analyses were carried out on an HPLC system from Waters (Milford, Mass.) model 501 equipped with a tunable UV-Vis detector model 484. $^1$H-NMR spectra were obtained on a 300 MHz NMR spectrometer Bruker (Westmont, Ill.) model Aspect 3000. Mass spectra data were obtained either on a Micromass AutoSpec (Beverly, Mass.) Mass Spectrometer using fast atom bombardment (FAB) as the ionization technique or on a Applied Biosystems (Foster City, Calif.) Mass Spectrometer model MDS Sciex API 365 using Electrospray (ESI) as the ionization technique. The cells were irradiated using a lab-built bank of four parallel 40 Watts tubular cold fluorescent light bulbs from Sylvania (Dania Beach, Fla.) model F40 CWP. The emission profile of this light source was characterized on a Timemaster Strobemaster fluorometer from Photon Technology International, Inc. (South Brunswick, N.J.), and its fluence rate (18 Watts/m$^2$) measured with a solid-state joulemeter model PM30VI from Molectron (Portland, USA). 1-octanol/water partition coefficients were determined at 25° C. using equal volumes of these two solvents pre-equilibrated with each other. Typically, five distinct dye solutions (~10 μM) were prepared in water and subsequently equilibrated with 1-octanol. After the equilibrium was reached, the aqueous and/or organic phases where equilibrated again with new aliquots of the second solvent of the respective 1-octanol/water solvent pair and the final dye concentration in the organic and aqueous phases determined by absorption spectroscopy. This re-partitioning procedure was repeated as needed to provide for a constant value of the partition coefficient in two subsequent 1-octanol/water equilibria. All partition coefficients were measured at neutral pH.

Preparation, purification, and characterization of $CV^+$ derivatives:

N,N,N',N',N''-pentamethylpararosaniline, N,N,N',N'-tetramethylpararosaniline, and N,N',N''-trimethylpararosaniline were prepared through the sequential oxidative N-dealkylation of $CV^+$ catalyzed by HRP. A description of this process may be found in Gadelha, et al., *Chem-Biol. Interact*, 85, 35–38 (1992), which is incorporated herein by reference. One of the major advantages of using this strategy is that, unlike chemical methods, the HRP-catalyzed reaction generates mostly selected isomers as reaction products. That is, while the reaction efficiently generates N,N,N',N''-tetramethylpararosaniline and N,N',N''-trimethylpararosaniline, it does not generate N,N,N',Nα-tetramethylpararosaniline and N,N',N'-trimethylpararosaniline in any significant (detectable) extent. The absence of isomers in the final reaction media facilitates the purification of the reaction products to the level required for a more detailed analysis of structure-activity relationships in in vitro assays. Typically, HRP (0.085 μM) and hydrogen peroxide (20.4 mg, 600 μmol) were sequentially added to a solution of Crystal Violet (60 mg, 147.1 μmol) in 500 mL of 10 mM sodium phosphate buffer pH 7.3. The reaction mixture was kept in the dark under continuous magnetic stirring and the reaction progress monitored by HPLC (reversed phase $C_{18}$ column; 90% Acetonitrile:10% 50 mM aqueous Perchloric Acid as eluent, UV/Vis analysis at 550 nm and 280 nm). After the reaction was complete, the reaction products were extracted from the aqueous media with 250 mL of n-butanol, the solvent removed by roto-evaporation, and the dyes of interest isolated by reduced pressure chromatography using columns packed with pre-treated silica gel. The chromatography procedure was performed as follows: 100 grams of 230–400 mesh Merck grade 9385 $SiO_2$ were washed with 250 ml of 1 M NaCl solution and subsequently filtered through a glass Buchner funnel under reduced vacuum. This pre-treated, water-deactivated, NaCl-equilibrated $SiO_2$ was then made into a slurry with 2-propanol and packed into 1.5 cm-diameter columns under reduced pressure (ca. 5–8 psi). The dye mixtures were dissolved in 2-propanol and the columns run under reduced pressure using this solvent as the mobile phase. The dye fractions (concentrated under vacuum) were subsequently analyzed by HPLC, and those containing highly purified dyes (>98% pure) were combined and dried under vacuum before storage under nitrogen in the dark.

As the amount of $H_2O_2$ available in the enzymatic reaction media is increased, the fourth, fifth, and sixth members of the $CV^+$ sequential N-dealkylation series are also produced in the HRP-catalyzed reaction (e.g. N,N'-dimethylpararosaniline, N-methylpararosaniline, and pararosaniline). However, it has been found that it is substantially more difficult to control this enzymatic process to generate these last three products of sequential CV⁺ dealkylation in high yields and high purity levels than it is to generate the first three dealkylation products. For this reason, N,N'-dimethylpararosaniline and N-methylpararosaniline were alternatively prepared through the sequential N-methylation of commercially available pararosaniline using iodomethane as the alkylating agent. Typically, 10 ml of iodomethane (160 mmol) were slowly added to 40 ml of a stirred methanol solution of pararosaniline (0.813 g, 2.51 mmol), the reaction mixture kept under reflux and the reaction progress followed by HPLC (reversed phase $C_8$ column; 70% acetonitrile:30% 20 mM aqueous $NH_4Cl$ as eluent, UV/Vis analysis at 550 nm and 280 nm). The final reaction products were subsequently dried through roto-evaporation and separated using open column chromatography. In this case, activated $SiO_2$ (230–400 mesh) columns were slurry packed in 70% $CHCl_3$/30% 2-propanol with 20 mM HCl. These columns were run under gravity flow using the same solvent system used for their packing.

Mass spectrometry and $^1$H-NMR data for the new compounds are the following: N,N,N',N',N"-pentamethylpararosaniline, FAB-MS (m/z) for $C_{24}H_{28}N_3$, calcd, 358.5. obsd, 358.2. $^1$H-NMR (DMSO-d6) δ (ppm): 8.28 (m, 1H), 7.26 (m, 6H), 6.99 (d, 4H, J=9.0 Hz), 6.86 (d, 2H, J=8.8 Hz), 3.21 (s, 12H), 2.93 (d, 3H, J=4.8 Hz). N,N,N',N"-tetramethylpararosaniline, FAB-MS (m/z) for $C_{23}H_{26}N_3$: calcd, 344.5. obsd, 344.1. $^1$H NMR (DMSO-d6) δ (ppm): 8.17 (m, 2H), 7.25 (m, 6H), 6.98 (d, 2H, J=7.9 Hz), 6.84 (d, 4H, J=8.43), 3.20 (s, 6H), 2.92 (d, 6H, J=3.87 Hz). N,N',N"-trimethylpararosaniline, FAB-MS (m/z) $C_{22}H_{24}N_3$, calcd, 330.5. obsd, 330.2. $^1$H NMR (DMSO-d6) δ (ppm): 8.19 (bs, 3H), 7.22 (d, 6H, J=8.8 Hz), 6.84 (d, 6H, J=8.8), 2.90 (bs, 9H). N,N'-dimethylpararosaniline, FAB-MS (m/z) for $C_{21}H_{22}N_3$, calcd, 316.4. obsd, 316.2. $^1$H NMR (DMSO-d6) δ (ppm): 8.23 (bs, 2H), 7.49 (bs, 2H), 7.20 (m, 6H), 6.82 (m, 6H), 2.90 (s, 6H). N'-methylpararosaniline, ESI-MS (m/z) for $C_{20}H_{20}N_3$: calcd, 302.4. obsd, 302.4.

The Biological Model:

HT-29 human colon adenocarcinoma cells (ATCC HTB-38) and CV-1 green monkey kidney cells (ATCC CCL-70) were obtained from the American Type Culture Collection (Manassas, Va.). Both cell lines were grown in RPMI 1640 media supplemented with 10% FBS, amphotericin B (0.63 μg/ml), penicillin (200 units/ml) and streptomycin (200 μg/ml). Small petri dishes (35 mm in diameter) were seeded at low cell densities (9×10⁵ cells per 3 ml of growth media) to provide for the formation of evenly distributed monolayers and the cells were allowed to attach overnight. Before irradiation, the cells were washed twice with fresh Dulbecco's phosphate-buffered saline (DPBS) solution and subsequently incubated for 60 minutes at 37° C. in the presence of 3 ml of 5 μM TAM⁺ dye solution prepared in fresh phosphate buffer saline (PBS). The original TAM⁺ stock solutions were prepared in ethanol, and the final ethanol content in the PBS solutions used for cell incubation was always kept at the 1% level. After incubation in the presence of the TAM⁺ dye, the cells were washed twice with DPBS, re-incubated with 3 ml of PBS, and immediately subjected to irradiation. During irradiation, the cells were kept at approximately 20 cm from the bank of cold fluorescent lamps and at room temperature. After irradiation, the PBS was replaced by fresh growth media and the cells incubated for 24 hours before being fixed with methanol and stained with a 0.1% aqueous CV⁺ solution. In a series of experiments designed to explore the effect of EV⁺ concentration on tumor selectivity, after this last 24 hours incubation in fresh growth media the cells were detached from the culture dishes with trypsin/EDTA in PBS and the survival ratio estimated using the trypan blue dye exclusion test as described in Perry et al., *Biotechniques*, 22, 1102–1106, Biotechniques (1997), which is incorporated herein by reference. The imaging of the cells was carried out on a microscope from Nikon (Chicago, Ill.) model UFX-II equipped with a Nikon camera model FX35A.

Selective Phototoxicity Studies:

A model pre-clinical study to explore the selective phototoxicity of the TAM⁺ dyes towards tumor cells was conducted. These studies are described in detail in Indig et al., *Photochem. Photobiol. Sci.*, 1, 309–314 (2002), which is incorporated herein by reference. To this end, the phototoxicity of these dyes against adenocarcinoma (HT-29) and normal kidney cells (CV-1) was investigated. These cells were previously employed by Oseroff and co-workers in investigations designed to demonstrate that the differences in mitochondrial membrane potential typically observed between tumor and normal cells can be explored for phototherapeutic purposes. See Modica-Napolitano, et al., *Cancer Res.*, 58, 71 (1998); Koya, et al., *Cancer Res.*, 56, 538 (1996); Baptista, et al., *J. Phys. Chem.*, 102B, 4678 (1998). One of the major advantages of exploring the concept of mitochondrial targeting using this biological model rests on the fact that it provides for rapid visual inspection of whether a particular photosensitizer displays selective phototoxicity towards tumor cells. It also permits the timely and inexpensive analysis of structural determinants of tumor cell selectivity on the basis of relatively large numbers of photosensitizers.

FIG. 1 shows the relative phototoxicity of 10 distinct TAM⁺ dyes towards HT-29 and CV-1 cells. In these comparative experiments, half of the dye-loaded cell population present in each distinct petri dish was irradiated with cold fluorescent light, while the other half was protected from the incident irradiation by masking half of each petri dish with aluminum foil and black tape. In FIG. 1, the left half of each panel shows the area of each cell colony exposed to light, and the right-half, the area protected from the incident irradiation. Marked differences in cell density between the left and right sides in any one of the panels indicates that substantial phototoxicity is associated with the respective dye towards that cell line. If no significant phototoxicity is observed, the cell density in the left and right-halves of the cell colony is equivalent (visually undistinguishable).

A dye exhibits tumor selectivity when the exposure to light causes significant differences between the left (exposed) and right (unexposed) sides of the HT-29 plates but leaves the left and right sides of the CV-1 plates indistinguishable. For example, CV⁺ is found to be selective for tumor cells because it efficiently mediates the photoinduced destruction of HT-29 cells but does not damage the CV-1 cells. On the other hand, EV⁺ indiscriminately destroys the light-exposed colonies of both cell types, indicating that it is not selective for tumor cells. Relatively harsh conditions in the experiments presented in FIG. 1 were used to allow for straightforward visual inspection of tumor selectivity. Under these conditions, the phototoxic effects of the TAM⁺ dyes on tumor cells were maximized such that pronounced differences in cell density between the left and right-half of HT-29 plates could be observed.

FIG. 2 shows the absorption spectra (in water) of all the TAM⁺ dyes used in this study, along with the emission profile of the light source used to produce the data presented in FIG. 1. Note that although the overlaps between the absorption spectrum of each TAM⁺ dye and the emission profile of the light source used to irradiate the cells are different from each other, these differences do not negatively impact this qualitative analysis. As long as the absorption spectra of the photosensitizers of interest show substantial overlap with the emission profile of the light source, it is generally straightforward to optimize dye concentration, incubation time, and irradiation time to permit the simultaneous qualitative evaluation of a large number of photosensitizers with regard to tumor selectivity.

Lipophilic Character Studies:

In this study, the lipophilic character of the $TAM^+$ dyes was evaluated by measuring their 1-octanol/water partition coefficient (P), as described in Leo et al, *Chem. Rev.*, 71, 525–616 (1971), which is incorporated herein by reference. The higher the value of P in FIG. 1, the higher the lipophilic character of the TAM dye. The results presented in FIG. 1 show that selective phototoxicity of $TAM^+$ dyes towards tumor cells is observed for $CV^+$ and its N-dealkylated derivatives (compounds I to VII in FIG. 1). However, those dyes with increased lipophilic character, i.e. $EV^+$, $VPBBO^+$, and $VBR^+$ lose this selectivity. The observation that only those $TAM^+$ dyes with low values of 1-octanol/water partition coefficient are selective for tumor cells strongly suggests that this selective tumor toxicity is largely modulated by the reduced tendency of these more hydrophilic $TAM^+$ dyes to partition into lipophilic subcellular compartments. This inference is supported by previous work by Chen on the determinants of subcellular distribution of Rhodamine dyes. Chen demonstrated that the mechanism of cellular uptake and mitochondrial accumulation of Rhodamine-123 ($Rh-123^+$) is primarily controlled by mitochondrial membrane potentials. Accordingly, $Rh-123^+$ stains the cell mitochondria with virtually absolute selectivity, and is typically taken up in larger amounts and retained for longer periods by tumor cells as compared to normal cells. It is reasonable to infer that the mechanisms of cellular uptake and retention of $CV^+$ and its N-dealkylated analogs (compounds I to VII in FIG. 1) is also primarily controlled by mitochondrial membrane potentials, given that the 1-octanol/water partition coefficients associated with these dyes (2.2<P<0.21, see FIG. 1) are very close to the value associated with the highly specific mitochondrial marker $Rh-123^+$ (P=0.24). The inference that $CV^+$ and its N-demethylated analogs stain energized mitochondria with a high degree of specificity is in keeping with the observed tumor selectivity associated with the phototoxic effects of these dyes, since the higher mitochondrial membrane potentials typical of tumor cells would provide for a higher phototoxicity towards these cells as compared to normal cells. See Indig, et al., *J. Pharm. Sci.*, 89, 33–99 (2000).

The contribution of lipophilic partitioning on the mechanism of cellular uptake, subcellular distribution, and cellular retention of the more lipophilic $TAM^+$ dyes, namely $EV^+$ (P=237), $VPBBO^+$ (P=180), and $VBR^+$ (P=39) is bound to be much more pronounced for these dyes than for $CV^+$ and its more hydrophilic N-demethylated analogs. Because the more lipophilic $TAM^+$ dyes are expected to partition into a variety of lipophilic subcellular compartments with equivalent efficiencies in both tumor and normal cells, their putative enhanced accumulation in the mitochondria of tumor cells no longer results in any significant selective phototoxicity. That is, in these cases, the equivalent photoinduced destruction of a variety of subcellular compartments other than the mitochondria in tumor and normal cells precludes tumor selectivity, regardless of whether the mitochondria of the tumor cells are more efficiently destroyed upon irradiation than the mitochondria of normal cells.

The hypothesis that a highly specific mitochondrial localization of cationic photosensitizers is a major prerequisite for tumor selectivity is supported by previous investigations of the subcellular distribution of $CV^+$ and $EV^+$ in rat basophilic leukemia (RBL) cells. See Indig et al., *J. Pharm. Sci.*, 89, 88–99 (2000). In that study, multi-photon laser scanning microscopy was used to obtain simultaneous images of the fluorescence of NAD(P)H (an endogenous mitochondrial marker), $Rh-123^+$ and $CV^+$ or $EV^+$ in RBL cells incubated in the presence of both $Rh-123^+$ and one of these $TAM^+$ dyes. While the comparison of the subcellular distribution of the NAD(P)H, $Rh-123^+$, and $TAM^+$ fluorescence clearly indicated that $CV^+$ does localize in the mitochondria with a high degree of specificity, the results obtained for $EV^+$ indicated otherwise. The spatial distribution associated with the fluorescence of $EV^+$ in RBL cells was consistent with its heavy accumulation not only in the mitochondria but also in other subcellular compartments, presumably as a result of a higher contribution of the partition phenomena on the mechanism of subcellular distribution of $EV^+$ as compared to $CV^+$.

These imaging experiments indicated that while $EV^+$ is expected to mediate the photochemical damage of a variety of distinct subcellular compartments in tumor and normal cells with comparable efficiency, $CV^+$ is expected to induce little or no photoinduced damage towards any subcellular compartment other than the mitochondria. In addition, to explore whether a decrease in the intracellular concentration of the most lipophilic $TAM^+$ photosensitizer considered here ($EV^+$) might lead to a more specific mitochondrial accumulation, and therefore provide the conditions required for tumor selectivity to take place, the phototoxicity of $EV^+$ towards tumor and normal cells as a function of its concentration in the incubation media was compared. As expected, the phototoxic effects towards both CV-1 and HT-29 cells decrease upon decreasing $EV^+$ concentration (5.0 $\mu$M, 1.0 $\mu$M, 0.5 $\mu$M, and 0.1 $\mu$M), but no significant tumor selectivity even for the most diluted $EV^+$ solutions was observed. For example, upon 90 minutes irradiation of cells incubated for one hour with 0.1 $\mu$M $EV^+$ solutions, the fraction of cells killed was found to be 32±4% for the case of CV-1 cells and 30±2% for the case of HT-29 cells. Therefore, these observations strongly suggest that the success of the concept of mitochondrial targeting in (photo)chemotherapy of neoplastic diseases rests not only on the preferential accumulation and retention of certain cationic drugs in the mitochondria of tumor cell as compared to normal cells, but on their close to absolute specificity towards this organelle.

EXAMPLE 3

Preferential Destruction of Adenocarcinoma Cells by Halogenated Triarylmethane Dyes To explore whether a heavy-atom substitution in tumor-selective triphenylmethane dyes would generate a new class of phototoxic compounds still showing tumor selectivity, bromo-derivatives of crystal violet, methyl violet 2B, and basic fuchsin were prepared and tested. The results reported below demonstrate that in these triphenylmethane dyes the structural changes associated with the heavy-atom substitution do not undermine tumor selectivity. All new brominated dyes described below were found to be both tumor-selective and highly phototoxic towards tumor cells. Heavy-atom substituted, tumor-selective phototoxic compounds represent a new class of drugs with potential also in combined modalities of cancer therapy. For example, upon light exposure of a tumor loaded with a phototoxic agent displaying a radioative atom in its molecular structure, the toxic effects associated with the phototherapeutic procedure would add to the toxic effects associated with the emission of ionizing radiation by the radioactive isotope.

Also described below are exemplary methods for the preparation and evaluation of a more rigid derivative of crystal violet, having the scaffold structure shown in Formula II. This new compound strongly absorbs light in the 750–900 nm region of the spectrum. In this spectroscopic region light penetration into living tissue is close to maximal. Therefore, this compound shows spectroscopic characteristics that are well suited for the treatment of relatively large solid tumors, which require deep penetration of the exciting light into the tumoral mass. Heavy-atom derivatives of this more rigid crystal violet analog are also suitable for use in tumor imaging and molecular radiation therapy, that is, as new agents for nuclear medicine.

Materials and Methods:
Reagents and Cell Culture Media:

Basic fuchsin ($BF^+$), methyl violet 2B ($MV2B^+$), ethyl violet ($EV^+$), acetic acid, acetonitrile, hydrochloric acid, perchloric acid, silica gel (230–400 mesh Merck grade 9385), methanol and octan-1-ol from Aldrich (Milwaukee, Wis.), bromine, sodium chloride, potassium chloride, sodium phosphate (dibasic), potassium phosphate (monobasic), ammonium hydroxide, crystal violet ($CV^+$), and trypan blue from Sigma Chemical Co. (St. Louis, Mo.), glycerol and propan-2-ol from Fisher Scientific (Pittsburgh, Pa.), and ethanol from Pharmaco Products, Inc. (Brookfield, Conn.) were, unless otherwise stated, of high purity grade and used as received. RPMI 1640 cell culture media, DPBS, fungizone (amphotericin B), penicillin, streptomycin, ethylenediaminetetraacetic acid (EDTA; tetrasodium salt) and trypsin (porcine) were obtained from Gibco (Rockville, Md.). Fetal bovine serum (FBS) was purchased from Atlanta Biologica (Norcross, Ga.). Water was distilled, deionized, and filtered prior to use (Millipore Milli-Q system; resistivity, 18 M$\Omega$ cm).

Instruments and Methods:

Spectrophotometric studies were performed with a Shimadzu UV-2101 PC spectrophotometer. High Performance Liquid Chromatography (HPLC) analyses were carried out on an HPLC system from Waters (Milford, Mass.) model 501 equipped with a tunable UV-VIS detector model 484. The $^1$H-NMR spectra were obtained using 400 MHz and 500 MHz spectrometers from Varian model UNITY INOVA. Mass spectra data were obtained either on an Applied Biosystems (Foster City, Calif.) mass spectrometer model MDS Sciex API 365 or on an Agilent 1100 HPLC-MSD SL quadrupole mass spectrometer using electrospray (ESI) as the ionization technique.

The cells were irradiated using a lab-built bank of six parallel 40 Watt tubular cold fluorescent light bulbs from Sylvania (Dania Beach, Fla.) model F40 CWP. The emission profile of this light source was characterized by directing its irradiation directly to the monochromator/detector system of a Timemaster Strobemaster fluorometer from Photon Technology International, Inc. (South Brunswick, N.J.) whose response was factory-calibrated to provide corrected emission spectra. The fluence rate (18 Watts/m$^2$) of this light source was measured with a solid-state joulemeter model PM30VI from Molectron (Portland, Oreg.). 1-octanol/water partition coefficients were determined at 25° C. using equal volumes of these two solvents pre-equilibrated with each other. Typically, six distinct dye solutions (~10 $\mu$M) were prepared in water and subsequently equilibrated with 1-octanol. After the equilibrium was reached, the aqueous and/or organic phases were equilibrated again with new aliquots of the second solvent of the respective 1-octanol/water solvent pair and the final dye concentration in the organic and aqueous phases determined by absorption spectroscopy. This re-partitioning procedure was repeated as needed to provide for a constant value of the partition coefficient in two subsequent 1-octanol/water equilibria. All partition coefficients were measured at neutral pH.

Preparation, Purification and Characterization of Brominated Triphenylmethane Dyes and 3,6-Bis-Dimethylamino-9-(4-Dimethylamino-Phenyl)-Fluoren-9-Ylium:

The chloride salts of 3'-bromocrystal violet ($CV^+$—Br), 3'-bromomethyl violet 2B ($MV2B^+$—Br), and 3-bromobasic fuchsin ($BF^+$—Br) were synthesized via treatment of the respective parent dye with molecular bromine. To this end, typically 10–40 $\mu$M solutions of bromine in methanol were slowly added to 10–20 $\mu$M dye solutions also prepared in methanol and kept at room temperature under continuous magnetic stirring, and the reaction progress monitored by HPLC (reversed phase C18 column; 90% acetonitrile–10% 50 mM aqueous perchloric acid used as eluent for the cases of $CV^+$—Br and $MV2B^+$—Br, and 70% acetonitrile–30% 20 mM aqueous ammonium chloride used as eluent for the case of $BF^+$—Br). Crystal violet (>98% pure) and basic fuchsin (>98% pure) were used as received from the suppliers, while methyl violet 2B (~40% pure) was purified by column chromatography before use. This chromatographic procedure was performed as follows: 100 grams of 230–400 mesh Merck grade 9385 SiO$_2$ were washed twice with 250 ml of 1 M NaCl solution and subsequently filtered through a glass Buchner funnel under reduced vacuum. This pre-treated, water-deactivated, NaCl-equilibrated SiO$_2$ was then made into a slurry with propan-2-ol and packed into 1.5 cm-diameter columns under reduced pressure (ca. 5–8 psi). The dye mixtures were dissolved in propan-2-ol and the columns run under reduced pressure using this solvent as the mobile phase. The dye fractions (concentrated under vacuum) were subsequently analyzed by HPLC, and those containing highly purified dyes (>98% pure) were combined and dried under vacuum before storage under nitrogen in the dark. Analogously, the final products of the bromination reactions were dried through roto-evaporation and purified using column chromatography. The purification of $CV^+$—Br and $MV2B^+$—Br was carried out using the same column and solvent system described above for the purification of commercially available MV2B+. $BF^+$—Br was purified using activated SiO$_2$ columns slurry packed and run in 80% chloroform-20% methanol under gravity. The dye fractions (concentrated under vacuum) were subsequently analyzed by HPLC, and those containing highly purified targeted monobrominated dyes (>98% pure) were combined and dried under vacuum before storage under nitrogen in the dark.

The synthesis of 3,6-bis-dimethylamino-9-(4-dimethylamino-phenyl)-fluoren-9-ylium (R—$CV^+$) was carried out as originally proposed in U.S. Pat. No. 3,344,189, which is incorporated herein by reference. Initially, 1.48 g (3.6 $\mu$mol) of crystal violet was dissolved in 29 ml of aqueous 85% H$_2$SO$_4$ and 1% phosphoric acid and the reaction mixture slowly heated and kept at 210° C. for 30 minutes. The reaction mixture was subsequently cooled to room temperature, poured onto the ice, and then partially neutralized (to pH~3) with 1 M aqueous ammonium hydroxide. Sodium hydrosulfite (10 mmol) was subsequently added to reduce the dye to its leuco form, and the reaction mixture neutralized (pH~7) with NH$_4$OH. The precipitate formed in this step was filtered, washed with water, and dried.

Subsequently, this precipitate was dissolved in hot toluene and the solution filtered in activated carbon. The removal of the solvent by roto-evaporation produced 0.45 g of partially purified leuco intermediate. This intermediate was subsequently oxidized with 0.3 g of lead peroxide in 50 ml of glacial acetic acid, and with the addition of sulfuric acid to this solution lead was precipitated as lead sulfate and removed by filtration. The filtered solution was finally neutralized with ammonium hydroxide, and the solvent removed by roto-evaporation. The targeted dye was then purified using the same column chromatography/HPLC method described above for the cases of $CV^+$—Br and $MV2B^+$—Br, but with smaller (2 cm×7 cm) NaCl-equilibrated silica gel columns.

Mass spectrometry and $^1$H-NMR data for the synthesized compounds are the following: $CV^+$—Br, ESI-MS (m/z) for $C_{25}H_{29}N_3Br$, calcd. 450.4 and 452.4, and obsd. 450.2 and 452.2 (1:1 ratio due to the bromine isotopes). $^1$H-NMR (acetone-$d_6$) δ (ppm) 3.09 (s, 6 H), 3.38 (s, 12 H), 7.14 (d, 4 H, J=9.5 Hz), 7.33 (d, 1 H, J=8.5 Hz), 7.39 (dd, 1 H, J=2.0 Hz, J=8.5 Hz), 7.47 (d, 4 H, J=9.5 Hz), and 7.57 (d, 1 H, J=2.0 Hz). $MV2B^+$—Br, ESI-MS (m/z) for $C_{24}H_{27}N_3Br$, calcd. 436.4 and 438.4. obsd. 436.1 and 438.1. $^1$H-NMR (methanol-$d_4$), δ (ppm) 3.04 (s, 3 H), 3.29 (s, 12 H), 6.90 (d, 1 H, J=8.8 Hz), 7.01 (d, 4 H, J=9.2 Hz), 7.34 (dd, 1 H, J=2.0 Hz, J=8.8 Hz), 7.39 (d, 4 H, J=8.8 Hz), and 7.49 (d, 1 H, J=2.0 Hz). $PA^+$-Br, ESI-MS (m/z) for $C_{19}H_{17}N_3Br$ is calcd. 366.3 and 368.3, and obsd. 366.1 and 368.1; $^1$H NMR (acetone-$d_6$) δ (ppm) 7.05 (d, 4 H, J=9.0 Hz), 7.18 (d, 1 H, J=8.5 Hz), 7.29 (dd, 1 H, J=2.0 Hz, J=8.5 Hz), 7.38 (d, 4 H, J=9.0 Hz), and 7.55 (d, 1 H, J=2.0 Hz). R—$CV^+$, ESI-M (m/z) for $C_{25}H_{28}N_3$ is calcd. 370.5 and obsd. 370.2; $^1$H-NMR (methanol-$d_4$) δ (ppm) 3.10 (s, 6 H), 3.28 (s, 12 H), 6.48 (dd, 2 H, J=2.4 Hz, J=9.2 Hz), 7.01 (d, 2 H, J=9.2 Hz), 7.28 (d, 2 H, J=2.4 Hz), 7.48 (d, 2 H, J=9.2 Hz), and 7.90 (d, 2 H, J=9.2 Hz).

The Biological Model:

HT-29 human colon adenocarcinoma cells (ATCC HTB-38) and CV-1 green monkey kidney cells (ATCC CCL-70) were obtained from the American Type Culture Collection (Manassas, Va.). These cells represent tumor (HT-29) and normal (CV-1) cells. Both cell lines were grown in RPMI 1640 media supplemented with 10% FBS, amphotericin B (0.63 μg/ml), penicillin (200 units/ml) and streptomycin (200 μg/ml). Small petri dishes (35 mm in diameter) were seeded at low cell densities ($9\times10^5$ cells per 3 ml of growth media) to provide for the formation of evenly distributed monolayers and the cells were allowed to attach overnight. Before irradiation, the cells were washed twice with fresh DPBS solution and subsequently incubated for 60 minutes at 37° C. in the presence of 3 ml of dye solution of appropriate concentration prepared in fresh phosphate buffered saline (PBS). The original $TAM^+$ stock solutions were prepared in ethanol, and the final ethanol content in the PBS solutions used for cell incubation was always kept at the 1% level. After incubation in the presence of the $TAM^+$ dye, the cells were washed twice with DPBS, re-incubated with 3 ml of PBS, and immediately subjected to irradiation.

During irradiation, the cells were kept at approximately 20 cm from the bank of cold fluorescent lamps and at room temperature. After irradiation, the PBS was replaced by fresh growth media and the cells incubated for 24 hours before being detached from the culture dishes with trypsin/EDTA in PBS and the survival ratio estimated using the trypan blue dye exclusion method. A description of this method is provided in Leo, et al., *Chem Rev.*, 71, 525 (1971), which is incorporated herein by reference. In a series of experiments designed to provide for the visual inspection of tumor cell selectivity, only half of the dye-loaded cell population present in each distinct petri dish was subjected to irradiation, while the second half was protected from the incident light by masking half of each petri dish with aluminum foil and black tape. In these cases, after the 24 hour re-incubation period with fresh growth media, the cells were fixed with methanol and stained with a 0.1% aqueous $CV^+$ solution. The imaging of these half-irradiated dishes was carried out on a microscope from Nikon (Chicago, Ill.) model UFX-II equipped with a Nikon camera model FX35A.

Selective Phototoxicity Studies:

A model pre-clinical study to explore whether the brominated triphenylmethanes and the more rigid crystal violet analog (R—$CV^+$) show selective phototoxicity towards tumor cells was conducted. To this end, the phototoxicity of these dyes against adenocarcinoma (HT-29) and normal kidney (CV-1) cells was compared.

Figure 3:
FIG. 3 shows a series of panels illustrating the phototoxicity of cationic dyes (photosensitizers) towards adenocarcinoma (HT-29) and normal, healthy (CV-1) cells. Marked differences in cell density between the left and right sides in any one of the panels indicates that substantial phototoxicity is associated with the respective dye towards that cell line. If no significant phototoxicity is observed, the cell density in the left and right-halves of the cell colony is equivalent (visually undistinguishable).

FIG. 3 shows the relative phototoxicity of 6 distinct dyes towards HT-29 and CV-1 cells. Colonies of HT-29 (left panels) and CV-1 (right panels) cells were incubated for 1 hour with the dye under investigation, washed, and irradiated for 1 hour. Twenty four hours after irradiation the cells were fixed with methanol and stained. Before irradiation, half of each petri dish was masked with black tape. The area protected from light is represented by the right-half of each panel. Marked differences in cell density between the left and right sides in any one of the panels indicates that substantial phototoxicity is associated with the respective dye towards that cell line. Upon irradiation, selective phototoxicity towards tumor cells (i.e., substantial destruction of tumor cells with negligible phototoxicity towards normal cells) was observed for the dyes displaying the $TAM^+$ motif in their molecular structure and partition coefficient lower than 6.1. [$EV^+$]=[Rh $123^+$]=5 μM, [$CV^+$—Br]=[$MV2B^+$—Br]=[$BF^+$—Br]=1 μM, [R—$CV^+$]=0.5 μM.

A dye exhibits tumor selectivity when the exposure to light causes significant differences between the left (exposed) and right (unexposed) sides of the HT-29 plates but leaves the left and right sides of the CV-1 plates indistinguishable. For example, $CV^+$—Br is found to be selective for tumor cells because it efficiently mediates the photoinduced destruction of HT-29 cells but does not damage the CV-1 cells. Tumor selectivity was also found for R—$CV^+$, $MV2B^+$—Br, and $BF^+$—Br. On the other hand, ethyl violet ($EV^+$) indiscriminately destroys the light-exposed colonies of both cell types, indicating that it is not selective for tumor cells. RH $123^+$ does not show any detectable phototoxicity against the cell lines tested here, even when the Rh $123^+$ loaded cells were exposed to light during 12 consecutive hours.

Figure 4:
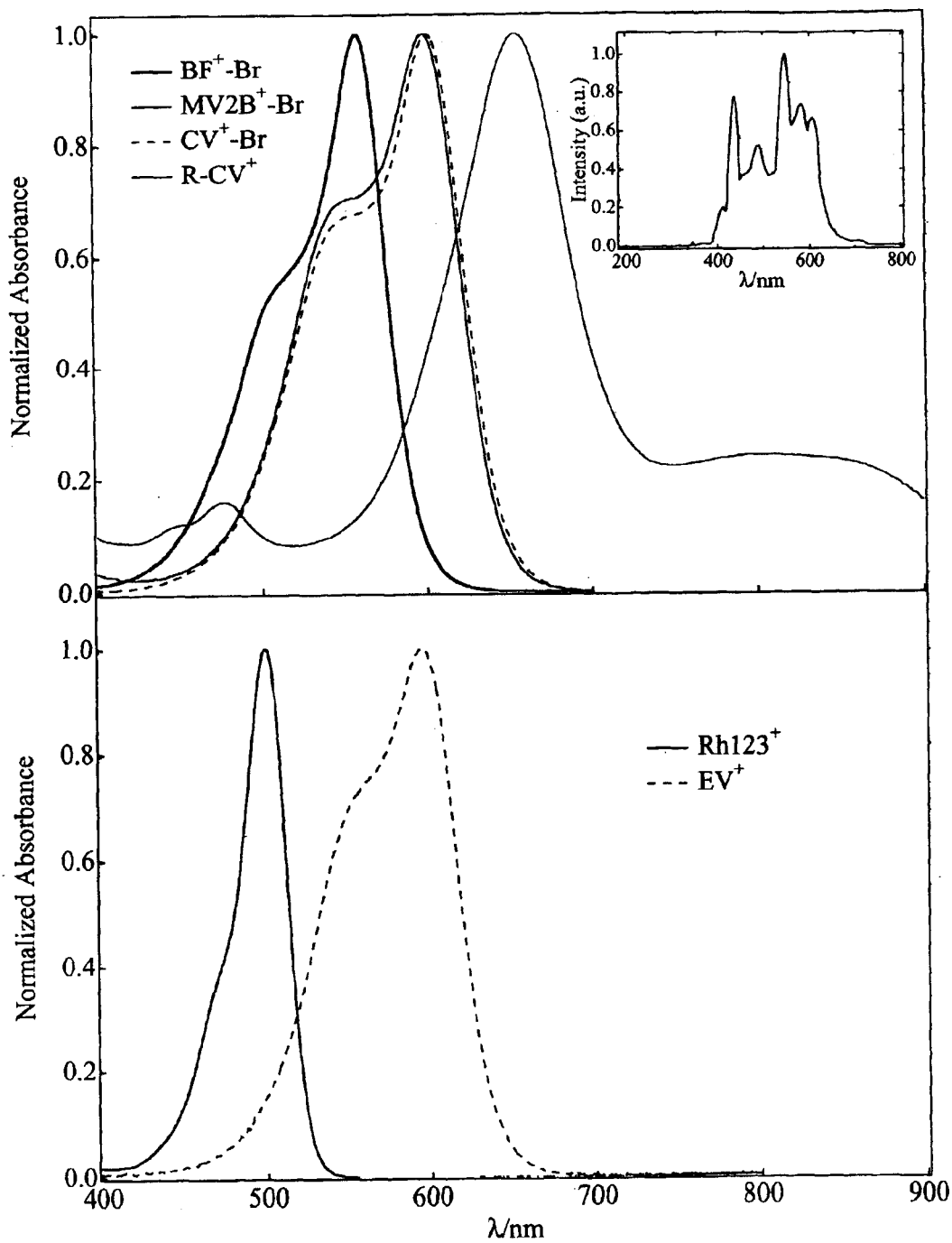
FIG. 4 shows absorption spectra of some of the cationic photosensitizers of this invention. Upper panel, from left to right at the wavelength of maximum absorption, bromobasic fuchsin (BF$^+$—Br), bromomethyl violet 2B (MV2B$^+$—Br), bromocrystal violet (CV$^+$—Br; dashed line), and 3,6-bis-dimethylamino-9-(4-dimethylamino-phenyl)-fluoren-9-ylium (R—CV$^+$). Inset: emission profile of the light source used to irradiate the cells. Lower panel, from left to right at the wavelength of maximum absorption, Rhodamine-123 (Rh 123$^+$) and ethyl violet (EV$^+$).
Figure 5:
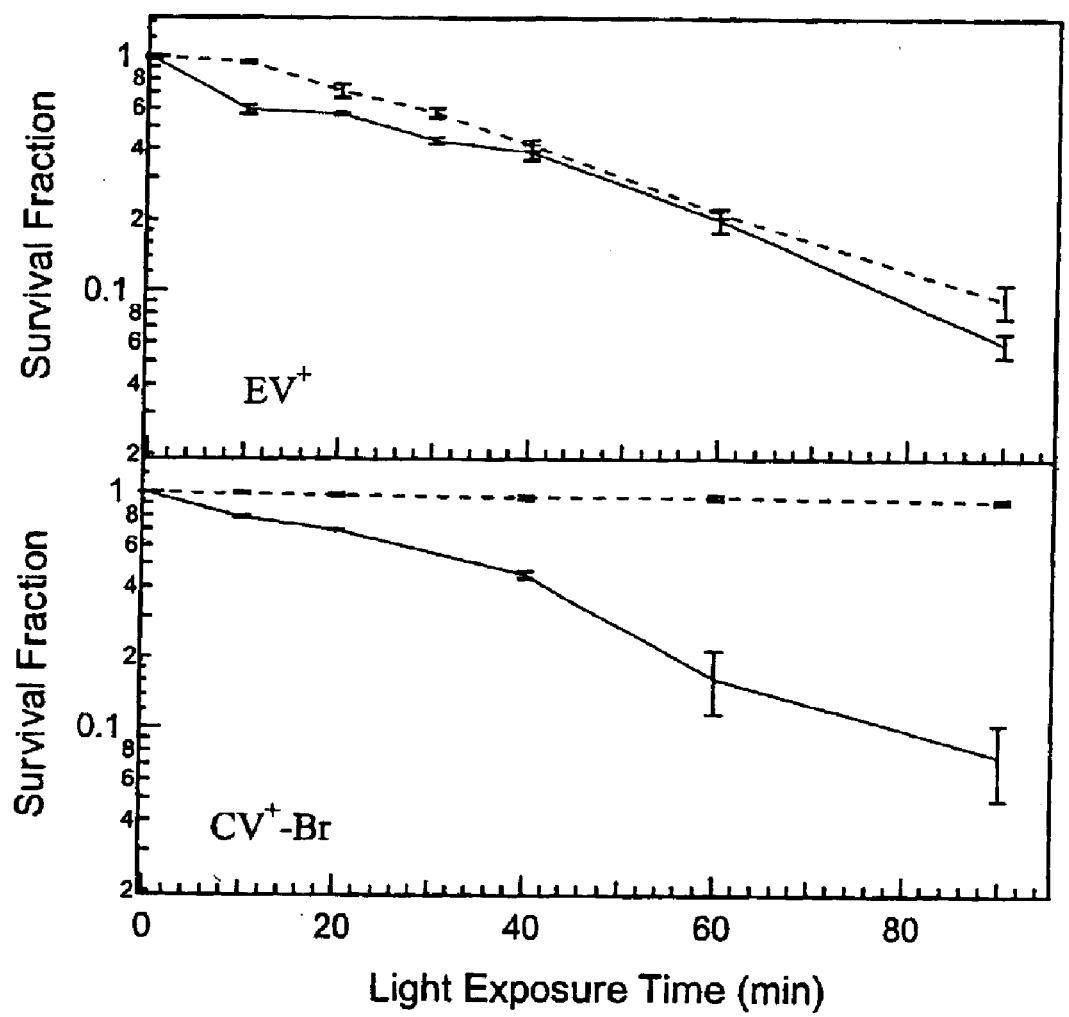
FIG. 5 shows photoinactivation of HT-29 cells (solid lines) and CV-1 cells (dashed lines) by ethyl violet (EV$^+$, upper panel) and bromocrystal violet (CV$^+$—Br, lower panel). [Dye]=1 $\mu$M.

FIG. 4 shows the absorption spectra of all dyes used in this study, along with the emission profile of the light source used to produce the data presented in FIG. 3. Although the overlap between the absorption spectrum of each dye and the emission profile of the light source used to irradiate the cells are different for each dye, these differences do not negatively impact the qualitative analysis shown in FIG. 3. As long as the absorption spectra of the photosensitizers of interest show substantial overlap with the emission profile of the light source, it is generally straightforward to optimize dye concentration, incubation time, and irradiation time to permit the simultaneous qualitative evaluation of a large number of photosensitizers with regard to tumor selectivity. The data shown in FIG. 5 represent a more rigorous comparison of the phototoxic effects of $EV^+$ and $CV^+$—Br against normal and tumor cells as a function of light exposure time.

Lipophilic Character Studies:

The lipophilic character of the dyes used in this study was evaluated by measuring their 1-octanol/water partition coefficient (P). The higher the value of P in FIG. 3, the higher the lipophilic character of the dye. The observation that among the phototoxic dyes only those with low values of 1-octanol/water partition coefficient are selective for tumor cells strongly suggests that this selective tumor toxicity is largely modulated by the reduced tendency of these more hydrophilic TAM$^+$ dyes to partition into lipophilic subcellular compartments. This inference is supported by the previous work by Chen on the determinants of subcellular distribution of Rhodamine dyes. See Chen, *Ann. Rev. Cell Biol.*, 4, 155 (1988). Chen demonstrated that the mechanism of cellular uptake and mitochondrial accumulation of Rh 123$^+$ is primarily controlled by mitochondrial membrane potentials. Accordingly, Rh 123$^+$ stains the cell mitochondria with high specificity, and is typically taken up in larger amounts and retained for longer periods by tumor cells as compared to normal cells. However, the photoreactivity of Rh 123$^+$ is very poor, and therefore this dye is not a good phototoxic agent. It is reasonable to infer that the mechanisms of cellular uptake and retention of the tumor-selective dyes described here are also primarily controlled by mitochondrial membrane potentials, given that the 1-octanol/water partition coefficients associated with these dyes (6.1>P>0.59, see FIG. 3) are very close to the value associated with the highly specific mitochondrial marker Rh 123$^+$ (P=0.24).

The contribution of lipophilic partitioning on the mechanism of cellular uptake, subcellular distribution, and cellular retention is bound to be much more pronounced for the more lipophilic dye (EV$^+$; P=237) than for the more hydrophilic dyes. Because the more lipophilic dye is expected to partition into a variety of lipophilic subcellular compartments with equivalent efficiencies in both tumor and normal cells, the equivalent photoinduced destruction of these subcellular compartments in tumor and normal cells precludes tumor selectivity, regardless of whether the mitochondria of the tumor cells are more efficiently destroyed upon irradiation than the mitochondria of normal cells.

As discussed in Example 2, above, it has been shown with respect to EV$^+$ that a decrease in the intracellular concentration of lipophilic dyes leads to a more specific mitochondrial accumulation and enhances tumor selectivity. These data strongly suggest that the success of the concept of mitochondrial targeting in photochemotherapy of neoplastic diseases rests not only on the preferential accumulation and retention of certain cationic drugs in the mitochondria of tumor cells as compared to normal cells, but on their close to absolute specificity towards this organelle.

The selective phototoxicity against tumor cells associated with the heavy-atom substituted triphenylmethane dyes considered here clearly demonstrates that this new class of phototoxic compounds shows structural features that enable them not only for use in photochemotherapy, but also as imaging agents and in novel modalities of cancer treatment based on the concept of molecular radiation therapy (that is, as new agents for nuclear medicine). Because the concept of mitochondrial targeting is based on a prevalent tumor cell characteristic, it is appropriate to anticipate that this new class of compounds will show selectivity towards a large variety of different tumors.

EXAMPLE 4

Preferential Destruction of Leukemia Cells by Halogenated Triarylmethane Dyes

Materials and Methods:
Reagents and Cell Culture Media:

The reagents and cell culture media were obtained and prepared as described in Example 3 with the exception of the following: Minimum Essential Medium (MEM) α medium was obtained from Life Technologies, Inc. (Rockville, Md.).

Instruments and Methods:

The spectroscopic studies and irradiation techniques were performed as described above in Example 3.

Preparation, Purification and Characterization of Brominated Crystal Violet:

The brominated crystal violet was prepared as described above in Example 3.

The Biological Model:

CV-1 green monkey kidney cells (ATCC CCL-70) and L1210 mouse lymphocytic leukemia cells (ATCC CCL-219) were obtained from the American Type Culture Collection (Manassas, Va.). CV-1 cells were grown and plated as described in example 3.

For the case of L1210 cells, 9×10$^5$ cells in 3 ml of MEM α medium supplemented with 10% FBS, penicillin (200 units/ml), streptomycin (200 μg/ml), amphotericin B (0.63 μg/ml), and sodium bicarbonate (2.2 g/l) were placed in small petri dishes (35 mm in diameter), and subsequently incubated with 3 ml of 5.0 μM CV$^+$—Br solution prepared in fresh phosphate buffered saline.

After incubation of the CV-1 and L1210 cells with the CV$^+$—Br solution, the cell colonies were exposed to light for a period of 90 minutes. During light exposure, the cells were kept at approximately 20 cm from the light source (a bank of cold fluorescent light bulbs).

After light exposure the cells were incubated for 24 hours in growth media and the survival rate finally estimated using the trypan blue dye exclusion assay.

Phototoxicity Studies:

The survival rates for CV-1 and L1210 cells observed in this experiment indicate that the phototoxic effects of CV$^+$—Br are highly selective towards the tumor cells. While the survival rate for the normal CV-1 cells was found to be 97%, the survival rate for the leukemia L1210 cells was found to be in the 22% range.

EXAMPLE 5

Preferential Destruction of Uterine Sarcoma Cells

Materials and Methods:
Reagents and Cell Culture Media:

The reagents and cell culture media were obtained and prepared as described in Example 3, with the exception of the following: McCoy's 5A medium was obtained from Signa Chemical Co. (St. Louis, Mo.).

Instruments and Methods:

The spectroscopic studies and irradiation techniques were performed as described above in Example 3.

Preparation, Purification and Characterization of Brominated Crystal Violet:

The brominated crystal violet was prepared as described above in Example 3.

The Biological Model:

MES-SA human uterine sarcoma cells [ATCC CRL-1976], MES-SA/Dx5 multiple drug resistant human uterine sarcoma cells [ATCC CRL-1977], and CV-1 green monkey kidney cells [ATCC CCL-70] were obtained from the American Type Culture Collection (Manassas, Va.). CV-1 cells were grown and plated as described in Example 3.

MES-SA and MES-SA/Dx5 cells were grown in McCoy's 5A media supplemented with 10% FBS, amphotericin B (0.63 μg/ml), penicillin (200 units/ml), streptomycin (200 μg/ml), and sodium bicarbonate (2.2 g/liter).

Small petri dishes (35 mm in diameter) were seeded with 9×10⁵ cells in 3 ml of growth media and the cells allowed to attach overnight. The colonies of CV-1, MES-SA and MES-SA/Dx5 were subsequently washed twice with fresh PBS and incubated for 60 minutes with 5 μm CV⁺—Br solutions prepared in fresh PBS.

After incubation in the presence of CV⁺—Br, the cells were exposed to light for a period of 90 minutes as described in examples 3 and 4. After irradiation the cells were washed, and incubated for 24 hours in fresh growth media before the survival rate was estimated using the trypan blue dye exclusion assay.

Phototoxicity Studies:

The results obtained in this experiment indicate that the phototoxic effects of CV⁺—Br are highly selective towards tumor cells. While the survival rate for the normal CV-1 cells was found to be 97%, the survival rate for the MES-SA cells was only 5%, and for the multiple drug resistant MES-SA/Dx5 cells the survival rate was found to be in the 40% range.

While preferred embodiments have been described, it should be understood that changes and modifications can be made therein in accordance with ordinary skill in the art without departing from the invention in its broader aspects as defined in the following claims.

What is claimed is:

1. A method of selectively killing cancer cells or selectively inhibiting the growth of cancer cells, comprising:
   (a) contacting a mixture comprising cancerous cells and non-cancerous cells with an effective amount of at least one compound having a structure represented by Formula I or Formula II:

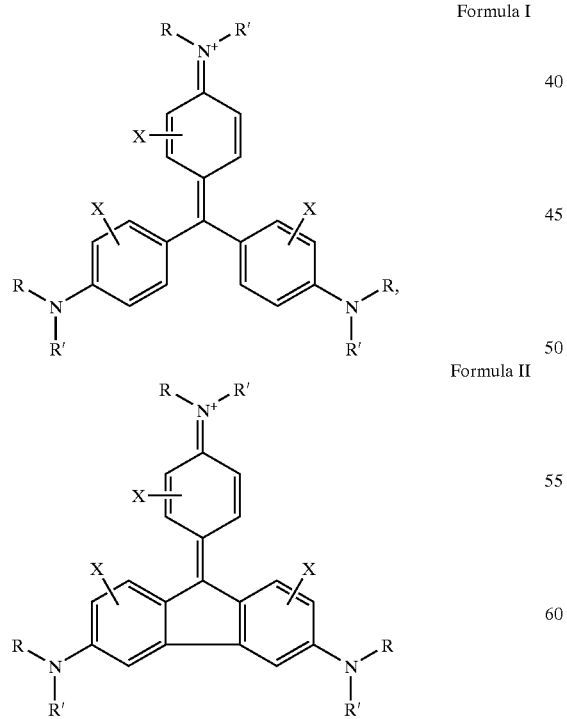

or pharmaceutically acceptable salts thereof, wherein each R and R' is independently selected from the group consisting of hydrogen atoms and substituted or unsubstituted $C_1$–$C_6$ linear or branched alkyl groups, further wherein each X is independently selected from the group consisting of hydrogen and halogen atoms, and still further wherein for compounds having the structure of Formula I, at least one X in the compound is a halogen atom; and
   (b) exposing the mixture comprising the cancerous cells and the non-cancerous cells from (a) to light of a suitable wavelength to photoactivate the at least one compound, wherein the cancerous cells are characterized in that the photoactivated compound exhibits selective phototoxicity toward the cancerous cells over the non-cancerous cells.

2. The method of claim 1, wherein at least one X in the at least one compound is a radio-opaque atom.

3. The method of claim 1, wherein at least one X in the at least one compound is a radioactive isotope of a halogen atom.

4. The method of claim 1, wherein one or more R or R' groups in the at least one compound are alkyl groups and further wherein the one or more R or R' groups are unsubstituted alkyl groups.

5. The method of claim 1, wherein the at least one compound is selected from a group of compounds consisting of:

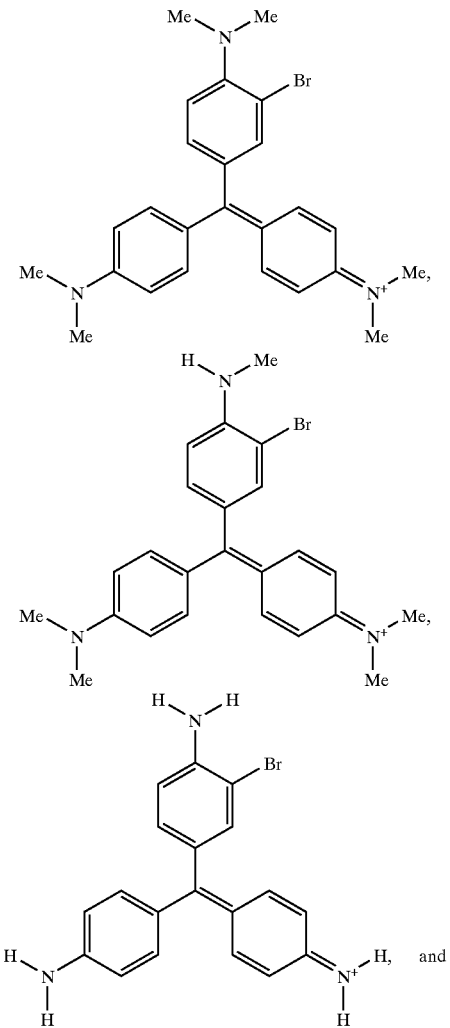

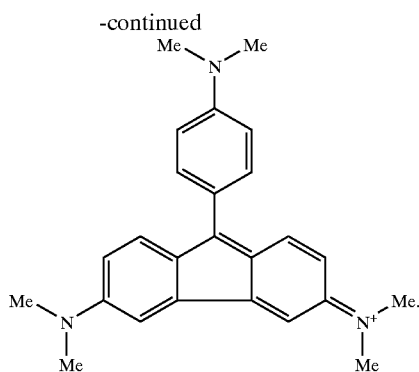

6. The method of claim 1, wherein the light of a suitable wavelength to photoactivate the at least one compound contains wavelengths in the range of from about 400 nm to about 750 nm.

7. The method of claim 1, wherein the light of a suitable wavelength to photoactivate the at least one compound contains wavelengths in the range of from about 750 nm to about 1000 nm.

8. The method of claim 1, wherein the mixture comprising the cancerous and the non-cancerous cells is exposed to light of a suitable wavelength to photoactivate the at least one compound for up to 90 minutes.

9. The method of claim 1, wherein the mixture comprising the cancerous cells and the non-cancerous cells comprises cancerous cells selected from the group consisting of leukemia cells, adenocarcinoma cells, and uterine sarcoma cells.

10. A compound, the compound comprising a structure represented by Formula I or Formula II:

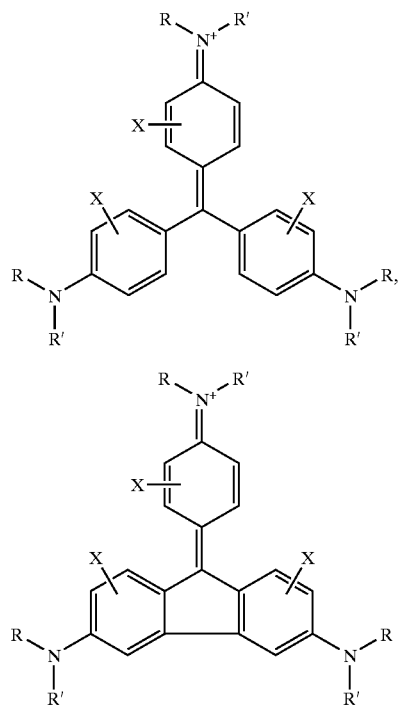

or salts thereof, wherein each R and R' is independently selected from the group consisting of hydrogen atoms and substituted or unsubstituted $C_1$–$C_6$ linear or branched alkyl groups, further wherein each X is independently selected from the group consisting of hydrogen and halogen atoms, and still further wherein at least one X in the compound is a halogen atom.

11. The compound of claim 10, wherein at least one X in the at least one compound is a radio-opaque atom.

12. The compound of claim 10, wherein at least one X in the at least one compound is a radioactive isotope.

13. The method of claim 10, wherein one or more R or R' groups in the at least one compound are alkyl groups and further wherein the one or more R or R' groups are unsubstituted alkyl groups.

14. The compound of claim 10, wherein the compound is selected from the group consisting of:

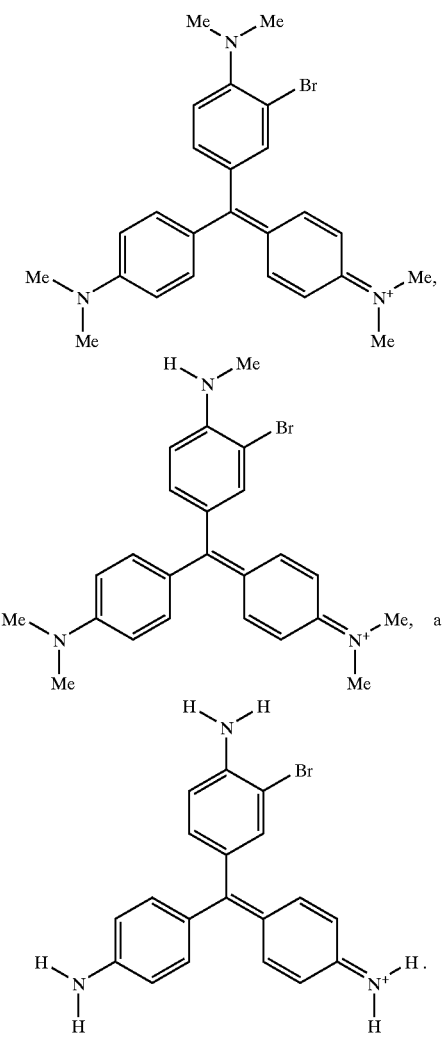

15. The compound of claim 10, wherein the at least one X in the compound is a bromine.

16. The compound of claim 10, wherein only one X is a halogen atom, and further wherein the halogen atom is either a bromine or an iodine.

17. The compound of claim 10, wherein each R and R' group is a hydrogen atom.

18. The compound of claim 10, wherein one R or R' group is a hydrogen atom and the other five R and R' groups are $C_1$–$C_6$ linear or branched alkyl groups.

19. The compound of claim 18, wherein the $C_1$–$C_6$ linear or branched alkyl groups are methyl groups.

20. The compound of claim 10, wherein each R and R' group is a $C_1$–$C_6$ linear or branched alkyl group.

21. The compound of claim 20, wherein the $C_1$–$C_6$ linear or branched alkyl groups are methyl groups.

22. A pharmaceutical composition comprising:

(a) a pharmaceutically effective amount of at least one compound having a structure represented by Formula I or Formula II:

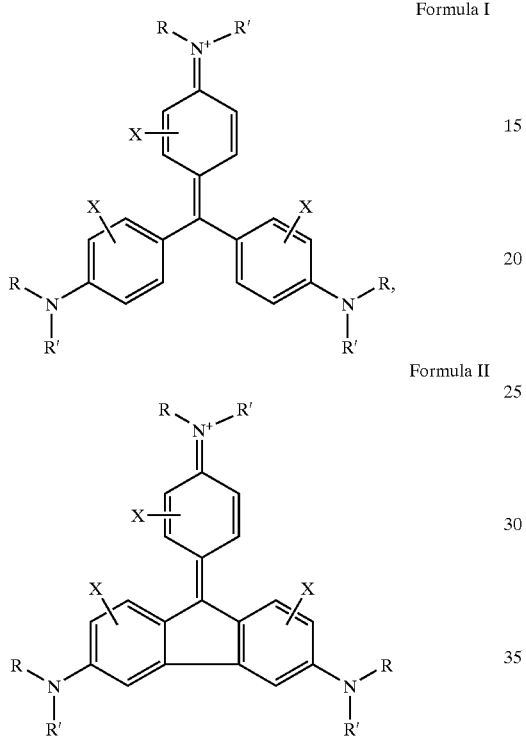

or pharmaceutically acceptable salts thereof, wherein each R and R' is independently selected from the group consisting of hydrogen atoms and substituted or unsubstituted $C_1$–$C_6$ linear or branched alkyl groups, further wherein each X is independently selected from the group consisting of hydrogen and halogen atoms, and still further wherein for compounds having the structure of Formula I, at least one X in the compound is a halogen atom; and (b) a pharmaceutically suitable amount of a carrier or diluent.

23. The pharmaceutical composition of claim 22, wherein at least one X in the at least one compound is a radio-opaque atom.

24. The pharmaceutical composition of claim 22, wherein at least one X in the at least one compound is a radioactive isotope.

25. The pharmaceutical composition of claim 22, wherein one or more R or R' groups in the at least one compound are alkyl groups and further wherein the one or more R or R' groups are unsubstituted alkyl groups.

26. The pharmaceutical composition of claim 22, wherein the at least one compound is selected from the group consisting of:

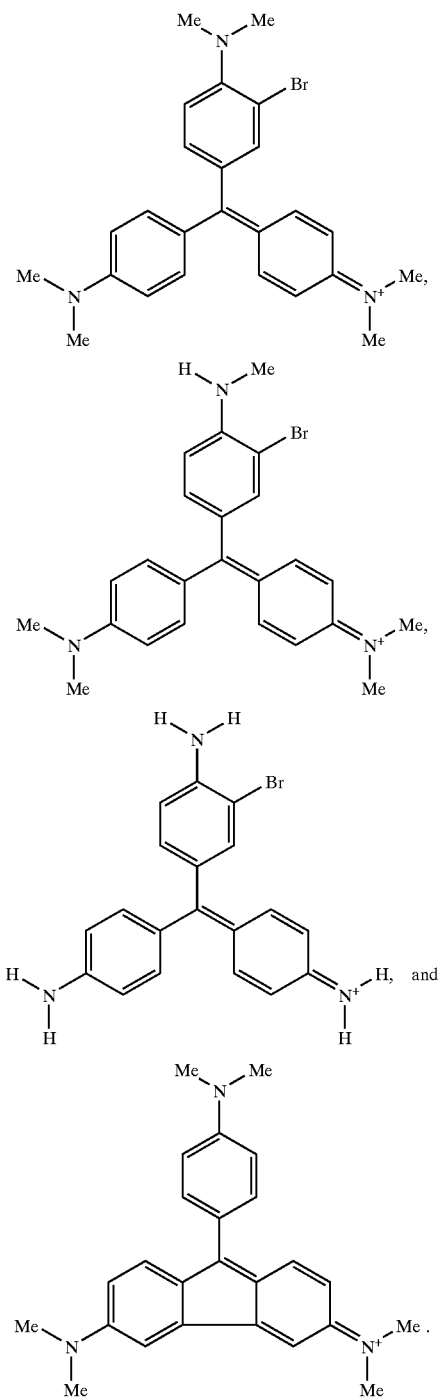

UNITED STATES PATENT AND TRADEMARK OFFICE
CERTIFICATE OF CORRECTION

PATENT NO. : 6,914,078 B2
DATED : July 5, 2005
INVENTOR(S) : Guilherme L. Indig

It is certified that error appears in the above-identified patent and that said Letters Patent is hereby corrected as shown below:

<u>Column 14,</u>
Lines 16-17, replace "N,N,N',N'-tetramethylpararosaniline," with
-- N,N,N',N''-tetramethylpararosaniline --.
Lines 27-28, replace "N,N,N',N∞-tetramethylpararosaniline" with
-- N,N,N',N'-tetramethylpararosaniline --.

Signed and Sealed this

Twenty-fifth Day of April, 2006

JON W. DUDAS
*Director of the United States Patent and Trademark Office*